(12) United States Patent
Takano et al.

(10) Patent No.: US 6,339,155 B1
(45) Date of Patent: Jan. 15, 2002

(54) PROCESS FOR PRODUCING 3-PHENYLURACIL COMPOUNDS

(75) Inventors: Minoru Takano, Kameoka; Hirofumi Mishima, Minoo, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/709,711

(22) Filed: Nov. 13, 2000

(30) Foreign Application Priority Data

Nov. 15, 1999 (JP) ............................................ 11-323797
Mar. 8, 2000 (JP) ......................................... 2000-063458

(51) Int. Cl.[7] ............................................ C07D 239/02
(52) U.S. Cl. ...................... 544/309; 544/314; 544/310; 544/311; 544/312; 544/105; 544/52
(58) Field of Search ................................ 544/314, 310, 544/309, 311, 312, 105, 52

(56) References Cited

U.S. PATENT DOCUMENTS

| 4,859,229 A | 8/1989 | Wenger et al. | ............... | 544/309 |
| 5,183,492 A | 2/1993 | Suchy et al. | ................. | 544/309 |

*Primary Examiner*—John M. Ford

(74) *Attorney, Agent, or Firm*—Sughrue, Mion, Zinn, Macpeak & Seas, PLLC

(57) ABSTRACT

The uracil compounds represented by the formula [V]:

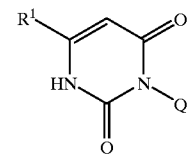

[V]

wherein $R^1$ represents C1–C5 perfluoroalkyl group and Q represents an aromatic group,
can be produced by making the amide compounds represented by the formula [II]:

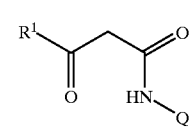

[II]

wherein $R^1$ and Q have the same meanings defined above, or its hydrate react with a cyanate salt in the presence of a protonic acid.

4 Claims, No Drawings

PROCESS FOR PRODUCING 3-PHENYLURACIL COMPOUNDS

FIELD OF THE INVENTION

The present invention relates to a process for producing 3-phenyluracil compounds.

BACKGROUND ARTS

It is described in U.S. Pat. No. 4,859,229, WO91/00278 and so on that the 3-phenyluracil compounds represented by the formula:

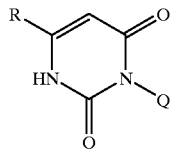

wherein R represents haloalkyl group and Q represents a substituted phenyl group,
and derivatives thereof have excellent herbicidal activity.

Some processes for producing 3-phenyluracil compounds are known. The processes given by the schemes 1 to 3 are known, with regard to the processes using the amide compound represented by the formula below:

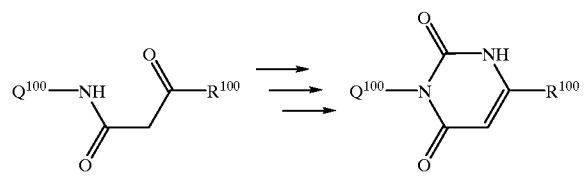

wherein $R^{100}$ represents optionally substituted alkyl group and $Q^{100}$ represents optionally substituted phenyl group, as a starting material.

Scheme 1
(described in PCT publication WO91/00278)

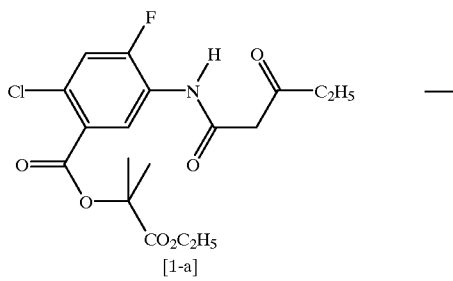

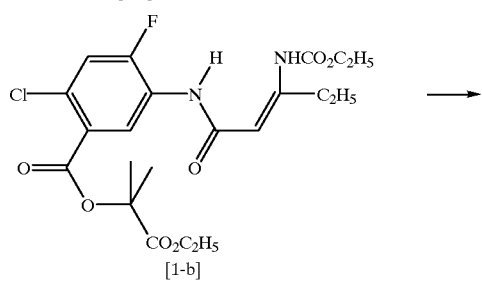

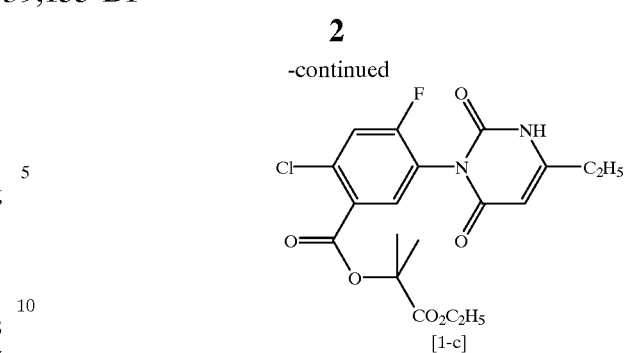

The process of Compound [1-a] to Compound [1-b] is carried out in an acidic condition using p-toluenesulfonic acid and the process of Compound [1-b] to Compound [1-c] is carried out in a basic condition using metal alkoxide.

Scheme 2
(described in PCT publication WO98/27067)

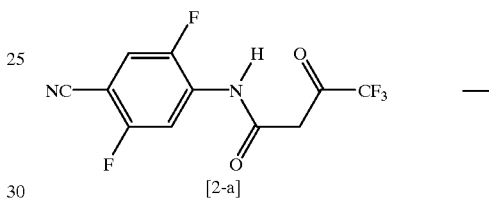

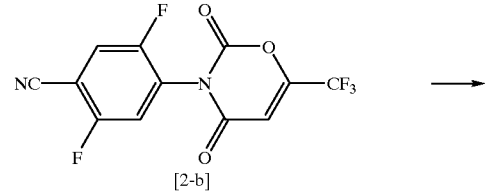

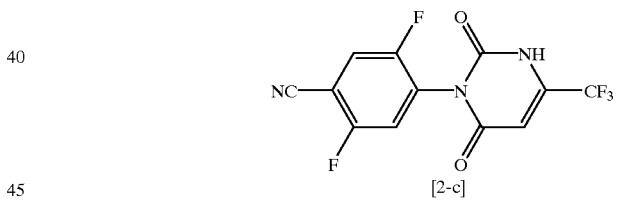

The process of Compound [2-a] to Compound [2-b] is carried out in a condition using phosgene/pyridine/4-dimethylaminopyridine and the process of Compound [2-b] to Compound [2-c] is carried out in a condition using aqueous ammonia.

Scheme 3
(described in PCT publication WO95/32952)

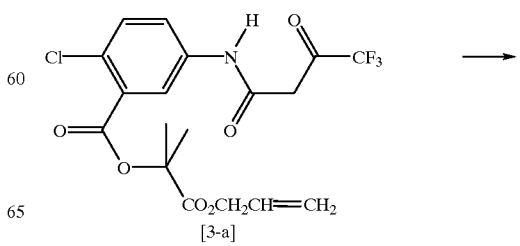

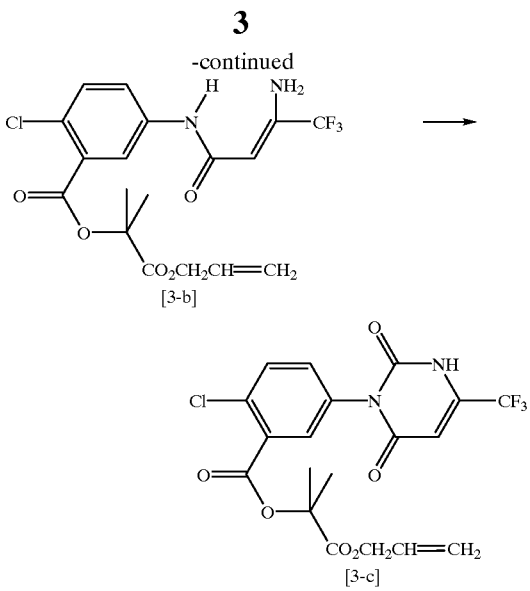

The process of Compound [3-a] to Compound [3-b] is carried out in a basic condition using anhydrous sodium acetate and the process of Compound [3-b] to Compound [3-c] is carried out in a condition using phosgene/pyridine/4-dimethylaminopyridine.

However, the intermediate compounds are required to be isolated, as every process shown by the schemes 1 to 3 is a 2-step reaction which is difficult to carry out the steps subsequently. Therefore, it is not sufficient process as an ecomonical one.

Under these circumstances, an economical process for producing the 3-phenyluracil compounds represented by the formula [V] that has a simple operation and high yield is desired to be developed.

SUMMARY OF THE INVENTION

The present invention provides a process for producing the 3-phenyluracil compounds represented by the formula [V]:

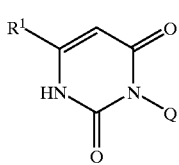

[V]

wherein $R^1$ represents C1–C5 perfluoroalkyl group and Q represents an aromatic group,
which comprises making the amide compound represented by the formula [II]:

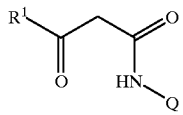

[II]

wherein $R^1$ and Q have the same meanings defined above, or its hydrate react with a cyanate salt in the presence of a protonic acid at 55° C. to 150° C.

The present invention provides an economical process for producing the 3-phenyluracil compounds because they can be produced in one-pot and in high yield.

DETAILED DESCRIPTION OF THE INVENTION

The process of the present invention is explained in detail. Typical process of the present invention is performed by adding a cyanate salt gradually into a mixture of an amide compound of the formula [II] or its hydrate and a protonic acid at 55° C. to 150° C. and allowing them to react.

The cyanate salt in the present invention means both of cyanate salts of a narrow meaning and isocyanate salts. Such cyanate salts of the narrow meaning are exemplified by alkali metal salts of cyanic acid (e.g., sodium cyanate, potassium cyanate). Examples of the isocyanate salt include silver isocyanate.

Examples of the protonic acid include aliphatic carboxylic acids such as acetic acid, propionic acid, butyric acid, trifluoroacetic acid and trichloroacetic acid; aromatic carboxylic acids such as benzoic acid and 4-nitrobenzoic acid; organic sulfonic acids such as p-toluenesulfonic acid, methanesulfonic acid and trifluoromethanesulfonic acid; inorganic mineral acids such as hydrochloric acid and sulfuric acid; and boronic acids such as phenylboronic acid.

The amount of the cyanate salt to be used in the present process is usually 1 mol to 10 mols, preferably 1 mol to 2 mols based on 1 mol of the amide compound given by the formula [II]. The amount of the protonic acid to be used in the present process is usually 1.1 mol to a large excess based on 1 mol of the amide compound given by the formula [II].

It is possible to utilize a solvent in the present process and the solvent that is inert in the present reaction condition can be used. Examples of the solvent include aliphatic hydrocarbons such as pentane, hexane, heptane, cyclopentane and cyclohexane; halogenated aliphatic hydrocarbons such as dichloromethane, chloroform and 1,2-dichloroethane; aromatic hydrocarbons such as benzene, toluene and xylene; halogenated aromatic hydrocarbons such as chlorobenzene and m-dichlorobenzene; ketones such as acetone, methyl ethyl ketone, methyl isobutyl ketone, cyclopentanone and cyclohexanone; ethers such as diethyl ether, tert-butyl methyl ether, diethylene glycol dimethyl ether, 1,4-dioxane and tetrahydrofuran; alcohols such as methanol, ethanol, propanol and 2-propanol; amides such as N,N-dimethyformamide and N,N-dimethylacetamide; sulfur-containing compounds such as dimethyl sulfoxide and sulfolane; nitro compounds such as nitromethane, nitroethane and 2-nitropropane; aliphatic nitrites such as acetonitrile; and mixtures thereof.

The present reaction is usually carried out in 30 minutes to 100 hours. It is preferable that the reaction mixture is kept under 50° C. at first and then aged at 55C to 150° C. after disappearance of most of the amide compound represented by the formula [II]. Thereafter, the reaction mixture is subjected to usual work-up procedures such as methods (a), (b), (c) and (d) to give the 3-phenyluracil compound represented by the formula [V].

(a) To concentrate the reaction mixture directly, wash with water and/or an organic solvent, and dry it.
(b) To pour the reaction mixture into water, neutralize with diluted acid such as diluted hydrochloric acid and diluted sulfuric acid, extract with an organic solvent, dry and concentrate it.
(c) To pour the reaction mixture into water, collect precipitated crystals by filtration and dry them.
(d) To cool the reaction mixture, collect precipitated crystals by filtration, wash with water and/or an organic solvent, and dry them.

The 3-phenyluracil compounds represented by the formula [V] can be purified by usual procedures such as recrystallization, column chromatography and so on.

The amide compounds represented by the formula [II] utilized in the present process can be prepared according to the known methods in U.S. Pat. No. 5,360,713, WO95/32952, WO98/27057 and WO98/27067, or prepared according to the preparation method described below: The production process by allowing an aniline compound given by the formula [III]:

[III]

wherein Q has the same meaning defined above, to react with an acetate ester compound given by the formula [IV]:

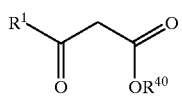

[IV]

wherein $R^1$ has the same meaning defined above and $R^{40}$ represents methyl group or ethyl group, in a solvent or without solvent.

The reaction temperature in said process is usually in the range of room temperature to 150° C., or room temperature to boiling point of a solvent utilized. Further, by-produced alcohol (methanol or ethanol) may be distilled away from the reaction mixture or a small amount of an acid or a base may be added for the purpose of speeding up the reaction.

The amount of the acetate ester compound, which is provided to the reaction, given by the formula [IV] is usually at the rate of 1 mol to 5 mols based on 1 mol of the aniline compound given by the formula [III].

Examples of the acid used for speeding up the reaction include protonic acids such as p-toluenesulfonic acid and methanesulfonic acid, and the amount of the used acid is at the rate of 0.05 mol to 1 mol based on 1 mol of the aniline compound given by the formula [1II]. Examples of the base include tertiary amines such as triethylamine, tributylamine and N,N-dimethylaniline; pyridines such as pyridine and picoline; and inorganic bases such as potassium carbonate and sodium hydride, and the amount of the used base is at the rate of 0.05 mol to 1 mol based on 1 mol of the aniline compound given by the formula [III].

Examples of the solvent include aliphatic hydrocarbons such as pentane, hexane, heptane, cyclopentane and cyclohexane; halogenated aliphatic hydrocarbons such as dichloromethane, chloroform and 1,2-dichloroethane; aromatic hydrocarbons such as benzene, toluene and xylene; halogenated aromatic hydrocarbons such as chlorobenzene and m-dichlorobenzene; ketones such as acetone, methyl ethyl ketone, methyl isobutyl ketone, cyclopentanone and cyclohexanone; ethers such as diethyl ether, tert-butyl methyl ether, diethylene glycol dimethyl ether, 1,4-whedioxane and tetrahydrofuran; amides such as N,N-dimethyformamide and N,N-dimethylacetamide; sulfur-containing compounds such as dimethyl sulfoxide and sulfolane; nitro compounds such as nitromethane, nitroethane and 2-nitropropane; aliphatic nitrites such as acetonitrile; and mixtures thereof.

After the reaction is completed, the reaction mixture is subjected to usual work-up procedures such as methods (a), (b) and (c) to give the objective product.
(a) To concentrate the reaction mixture directly, wash with water and/or an organic solvent, and dry it.
(b) To pour the reaction mixture into water, neutralize with aqueous saturated sodium bicarbonate and so on, extract with an organic solvent, dry and concentrate it.
(c) To pour the reaction mixture into water, collect precipitated crystals by filtration and dry them.

The produced amide compounds given by the formula [II] can be purified by the procedures such as recrystallization, column chromatography and so on.

The amide compound given by the formula [II] may exist as a hydrate which is formed by bonding one molecule of the amide compound with one molecule of water, and said compound can also be utilized to the process of the present invention. Said hydrate may have the chemical structure as follows:

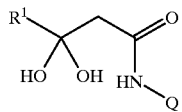

wherein $R^1$ and Q have the same meanings defined above.

The aniline compounds represented by the formula [III] can be prepared according to the methods in JP Sho62-221677A, JP Sho62-158280A, JP Sho63-156787A, EP-61741A, U.S. Pat. No. 4,670,046, U.S. Pat. No. 4,770,695, U.S. Pat. No. 4,709,049, U.S. Pat. No. 4,640,707, U.S. Pat. No. 4,720,297, U.S. Pat. No. 5,169,431, WO97/08136, WO98/13331, WO98/37065 and so on.

Typical examples of the aromatic group given by Q in the formulae [I], [II], [III], [IV] and [V] include optionally substituted phenyl group, optionally substituted pyridyl group, optionally substituted pyrazyl group, optionally substituted pyrimidinyl group, optionally substituted pyridazinyl group, optionally substituted triazinyl group, optionally substituted furyl group, optionally substituted thienyl group, optionally substituted pyrazolyl group, optionally substituted oxazolyl group, optionally substituted thiazolyl group, optionally substituted isoxazolyl group and optionally substituted isothiazolyl group. Preferable examples are optionally substituted phenyl group and exemplified by the groups given by the formulae Q1 to Q8 below:

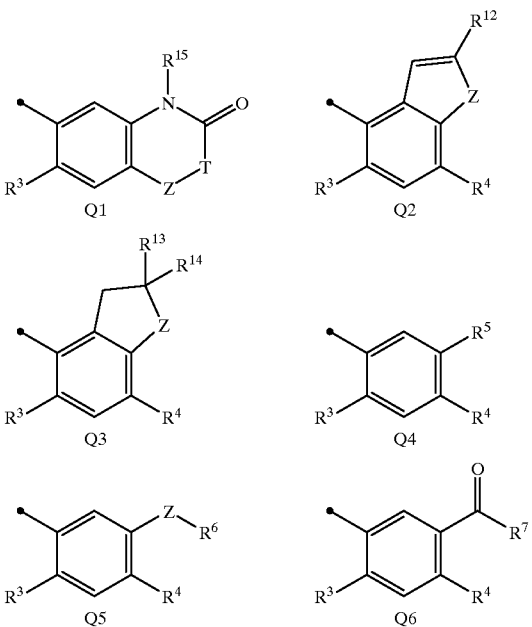

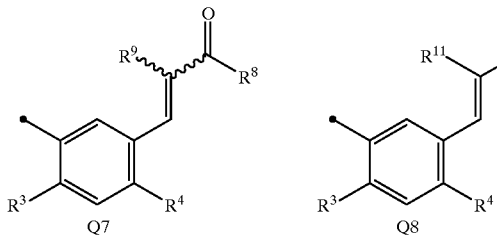

Q7           Q8

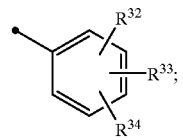

wherein R³ represents hydrogen atom or halogen atom; R⁴ represents hydrogen atom, halogen atom, cyano group, nitro group, ethynyl group or a group given by the formula:

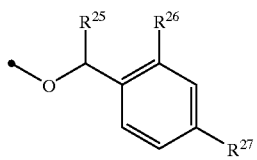

R⁵ represents hydrogen atom, C1–C6 alkyl group, halogen atom, cyano group, nitro group or hydroxy group; R⁶ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl)carbonyl group, (C1–C6 haloalkyl)carbonyl group, (C3–C8 cycloalkyl)carbonyl group, carboxy C1–C3 alkyl group, (C1–C6 alkoxy)carbonyl C1–C3 alkyl group, (C1–C6 haloalkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy)carbonyl (C1–C3 alkoxy)carbonyl C1–C3 alkyl group, (C1–C6 haloalkoxy)carbonyl (C1–C3 alkoxy) carbonyl C1–C3 alkyl group, (C3–C6 alkenyloxy)carbonyl (C1–C3 alkoxy)carbonyl C1–C3 alkyl group, (C3–C6 alkynyloxy)carbonyl (C1–C3 alkoxy)carbonyl C1–C3 alkyl group, (C3–C8 cycloalkoxy)carbonyl (C1–C3 alkoxy) carbonyl C1–C3 alkyl group, optionally substituted aryloxycarbonyl C1–C3 alkyl group, optionally substituted aryl (C1–C3 alkoxy)carbonyl C1–C3 alkyl group, (C1–C6 alkoxy)carbonyl group, or a group given by the formula —SO₂R¹⁷, —C(R²⁸)R²⁹CON(R²¹)R²², —C(R³⁰)R³¹COON(R²³)R²⁴,

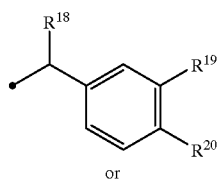

or

R⁷ represents hydrogen atom, C1–C6 alkyl group, C1–C6 haloalkyl group, C3–C8 cycloalkyl group, hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, carboxy C1–C3 alkoxy group, (C1–C6 alkoxy)carboxy C1–C3 alkoxy group, (C3–C8 cycloalkoxy)carboxy C1–C3 alkoxy group, (C3–C6 alkenyloxy)carboxy C1–C3 alkoxy group, (C3–C6 alkynyloxy)carboxy C1–C3 alkoxy group, optionally substituted phenoxy group, optionally substituted benzyloxy group, or a group given by the formula —N(R²¹)R²² or —ON(R²³)R²⁴; R⁸ represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the formula —N(R²¹)R²² or —ON(R²³)R²⁴; R⁹ represents hydrogen atom or halogen atom; R¹⁰ represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the formula —N(R²¹)R²² or —ON(R²³)R²⁴; R¹¹ represents hydrogen atom or halogen atom; R¹² represents hydrogen atom, formyl group, cyano group, nitro group, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy) carbonyl group, (C3–C8 cycloalkoxy)carbonyl group, (C3–C6 alkenyloxy)carbonyl group, (C3–C6 alkynyloxy) carbonyl group or C1–C3 alkoxy (C1–C3 alkoxy)carbonyl group; R¹³ represents hydrogen atom or C1–C3 alkyl group; R¹⁴ represents hydrogen atom, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy)carbonyl group, (C3–C8 cycloalkoxy) carbonyl group, (C3–C6 alkenyloxy)carbonyl group, (C3–C6 alkynyloxy)carbonyl group or C1–C3 alkoxy (C1–C3 alkoxy)carbonyl group; R¹⁵ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl)carbonyl group, (C1–C6 haloalkyl)carbonyl group, (C3–C8 cycloalkyl)carbonyl group, carboxy C1–C3 alkyl group, (C1–C6 alkoxy) carbonyl C1–C3 alkyl group, (C1–C6 haloalkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy)carbonyl (C1–C3 alkoxy)carbonyl C1–C3 alkyl group, (C1–C6 haloalkoxy)carbonyl (C1–C3 alkoxy) carbonyl C1–C3 alkyl group, (C3–C8 cycloalkoxy)carbonyl (C1–C3 alkoxy)carbonyl C1–C3 alkyl group, (C3–C6 alkenyloxy)carbonyl (C1–C3 alkoxy)carbonyl C1–C3 alkyl group, (C3–C6 alkynyloxy)carbonyl (C1–C3 alkoxy) carbonyl C1–C3 alkyl group, optionally substituted aryloxycarbonyl C1–C3 alkyl group, optionally substituted aryl (C1–C3 alkoxy)carbonyl C1–C3 alkyl group, (C1–C6 alkoxy)carbonyl group or a group given by the formula:

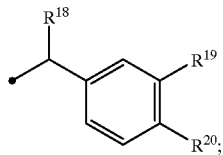

Z represents oxygen atom or sulfur atom; T represents direct bond or methylene group;

wherein $R^{17}$ represents C1–C3 alkyl group or C1–C3 haloalkyl group; $R^{18}$ represents hydrogen atom, C1–C3 alkyl group or (C1–C6 alkoxy)carbonyl group; $R^{19}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{20}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{21}$ and $R^{22}$ independently represent hydrogen atom or C1–C3 alkyl group, or combined together at their terminal ends to form C2–C5 alkylene group or (C1–C3 alkyleneoxy) C1–C3 alkylene group; $R^{23}$ and $R^{24}$ independently represent hydrogen atom or C1–C3 alkyl group, or combined together at their terminal ends to form C2–C5 alkylene group or (C1–C3 alkyleneoxy) C1–C3 alkylene group; $R^{25}$ represents hydrogen atom, C1–C3 alkyl group or (C1–C6 alkoxy) carbonyl group; $R^{26}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{27}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{28}$ represents hydrogen atom or C1–C3 alkyl group; $R^{29}$ represents hydrogen atom or C1–C3 alkyl group; $R^{30}$ represents hydrogen atom or C1–C3 alkyl group; $R^{31}$ represents hydrogen atom or C1–C3 alkyl group; $R^{32}$, $R^{33}$ and $R^{34}$ are the same or different and represent hydrogen atom, halogen atom, C1–C3 alkyl group, C1–C3 haloalkyl group, nitro group, hydroxy group, mercapto group, cyano group, carboxy group, (C1–C6 alkoxy)carbonyl group, (C3–C8 cycloalkoxy)carbonyl group, (C3–C6 alkenyloxy)carbonyl group, (C3–C6 alkynyloxy)carbonyl group, carboxy C1–C3 alkyl group, (C1–C6 alkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group, (C3–C6 alkynyloxy)carbonyl C1–C3 alkoxy group, carboxy C1–C3 alkylthio group, (C1–C6 alkoxy)carbonyl C1–C3 alkylthio group, (C3–C8 cycloalkoxy)carbonyl C1–C3 alkylthio group, (C3–C6 alkenyloxy)carbonyl C1–C3 alkylthio group, (C3–C6 alkynyloxy)carbonyl C1–C3 alkylthio group, C1–C6 alkoxy group, C3–C6 alkenyloxy group, C3–C6 alkynyloxy group, (C1–C6 alkyl)carbonyloxy group, (C1–C6 alkoxy)carbonyloxy group, C1–C6 alkylthio group, C3–C6 alkenylthio group, C3–C6 alkynylthio group, (C1–C6 alkyl)carbonylthio group, (C1–C6 alkoxy) carbonylthio group.

The substituents describd as "optionally substituted" above are exemlified by halogen atom, C1–C6 alkyl group, C1–C6 alkoxy group, C1–C6 haloalkyl group, C1–C6 haloalkoxy group, nitro group, cyano group, (C1–C6 alkoxy)carbonyl group, (C1–C6 alkoxy)carbonyl C1–C3 alkyl group and (C1–C6 alkoxy)carbonyl C1–C3 alkoxy group.

In the present invention, the C1–C5 perfluoroalkyl group represented by $R^1$ may include trifluoromethyl group and pentafluoroethyl group. The halogen atom represented by $R^3$ may include fluorine atom, chlorine atom, bromine atom and iodine atom. The halogen atom represented by $R^4$ may include fluorine atom, chlorine atom, bromine atom and iodine atom. The C1–C6 alkyl group represented by $R^5$ may include methyl group, ethyl group, propyl group, isopropyl group, butyl group, isobutyl group, sec-butyl group and tert-butyl group; and the halogen atom represented by $R^5$ may include fluorine atom, chlorine atom, bromine atom and iodine atom. The C1–C6 alkyl group represented by $R^6$ may include methyl group, ethyl group, propyl group, isopropyl group, butyl group, isobutyl group, sec-butyl group, tert-butyl group, pentyl group and hexyl group; the C1–C6 haloalkyl group represented by $R^6$ may include trifluoromethyl group, difluoromethyl group, 2-fluoroethyl group, 2-chloroethyl group and 2-bromoethyl group; the C3–C8 cycloalkyl group represented by $R^6$ may include cyclopropyl group, cyclobutyl group, cyclopentyl group and cyclohexyl group; the (C3–C8 cycloalkyl) C1–C3 alkyl group represented by $R^6$ may include cyclopropylmethyl group, cyclobutylmethyl group, cyclopentylmethyl group and cyclohexylmethyl group; the C3–C6 alkenyl group represented by $R^6$ may include allyl group, 1-methyl-2-propenyl group, 2-methyl-2-propenyl group and 1,1-dimethyl-2-propenyl group; the C3–C6 alkynyl group represented by $R^6$ may include propargyl group, 1-methy-2-propynyl group, 2-butynyl group and 1,1-dimethyl-2-propynyl group; the cyano C1–C3 alkyl group represented by $R^6$ may include cyanomethyl group, 1-cyanoethyl group, 2-cyanoethyl group and 1-methyl-2-cyanoethyl group; the (C1–C3 alkoxy) C1–C3 alkyl group represented by $R^6$ may include methoxymethyl group, 2-methoxyethyl group, ethoxymethyl group and 2-ethoxyethyl group; the (C1–C3 alkylthio) C1–C3 alkyl group represented by $R^6$ may include methylthiomethyl group, 2-ethylthioethyl group and 2-methylthioethyl group; the (C1–C6 alkyl)carbonyl group represented by $R^6$ may include acetyl group, propionyl group, butyryl group, isobutyryl group and pivaloyl group; the (C1–C6 haloalkyl)carbonyl group represented by $R^6$ may include trifluoroacetyl group, difluoroacetyl group, trichloroacetyl group and dichloroacetyl group; the (C3–C8 cycloalkyl)carbonyl group represented by $R^6$ may include cyclopropylcarbonyl group, cyclopentylcarbonyl group and cyclohexylcarbonyl group; the carboxy C1–C3 alkyl group represented by $R^6$ may include carboxymethyl group, 1-carboxyethyl group, 1-methyl-1-carboxyethyl group, 1-carboxypropyl group, 2-carboxyethyl group and 1-methyl-2-carboxylethyl group; the (C1–C6 alkoxy)carbonyl C1–C3 alkyl group represented by $R^6$ may include methoxycarbonylmethyl group, ethoxycarbonylmethyl group, propoxycarbonylmethyl group, isopropoxycarbonylmethyl group, butoxycarbonylmethyl group, isobutoxycarbonylmethyl group, sec-butoxycarbonylmethyl group, tert-butoxycarbonylmethyl group, pentyloxycarbonylmethyl group, isopentyloxycarbonylmethyl group, hexyloxycarbonylmethyl group, isohexyloxycarbonylmethyl group, 1-methoxycarbonylethyl group, 1-ethoxycarbonylethyl group, 1-(propoxycarbonyl)ethyl group, 1-(isopropoxycarbonyl)ethyl group, 1-(butoxycarbonyl)ethyl group, 1-(isobutoxycarbonyl)ethyl group, 1-(sec-butoxycarbonyl)ethyl group, 1-(tert-butoxycarbonyl)ethyl group, 1-(pentyloxycarbonyl)ethyl group, 1-(isopentyloxycarbonyl)ethyl group, 1-(hexyloxycarbonyl)ethyl group, 1-(isohexyloxycarbonyl)ethyl group, 1-methyl-1-(methoxycarbonyl)ethyl group, 1-methyl-1-(ethoxycarbonyl)ethyl group, 1-methyl-1-(propoxycarbonyl)ethyl group, 1-methyl-1-(isopropoxycarbonyl)ethyl group, 1-methyl-1-(butoxycarbonyl)ethyl group, 1-methyl-1-(isobutoxycarbonyl)ethyl group, 1-methyl-1-(sec-butoxycarbonyl)ethyl group, 1-methyl-1-(tert-butoxycarbonyl)ethyl group, 1-methyl-1-(pentyloxycarbonyl)ethyl group, 1-methyl-1-(isopentyloxycarbonyl)ethyl group, 1-methyl-1-(hexyloxycarbonyl)ethyl group and 1-methyl-1-(isohexyloxycarbonyl)ethyl group; the (C1–C6 haloalkoxy)carbonyl C1–C3 alkyl group represented by $R^6$ may include 2-fluoroethoxycarbonylmethyl group, 2-chloroethoxycarbonylmethyl group, 2-bromoethoxycarbonylmethyl group, 2,2,2-trifluoroethoxycarbonylmethyl group, 1-(2-fluoroethoxycarbonyl)ethyl group, 1-(2-chloroethoxycarbonyl)ethyl group, 1-(2-bromoethoxycarbonyl)ethyl group, 1-(2,2,2-trifluoroethoxycarbonyl)ethyl group, 1-methyl-1-(2-fluoroethoxycarbonyl) ethyl group, 1-methyl-1-(2-chloroethoxycarbonyl)ethyl group, 1-methyl-1-(2-bromoethoxycarbonyl)ethyl group and 1-methyl-1-(2,2,2-trifluoroethoxycarbonyl)ethyl group; the (C3–C8 cycloalkoxy)carbonyl C1–C3 alkyl group represented by $R^6$ may include cyclopropoxycarbonylmethyl group, cyclobutoxycarbonylmethyl group, cyclopentyloxycarbonylmethyl group, cyclohexyloxycarbonylmethyl group, 1-cyclopropoxycarbonylethyl group, 1-cyclobutoxycarbonylethyl group, 1-cyclopentyloxycarbonylethyl group, 1-cyclohexyloxycarbonylethyl group, 1-methyl-1-(cyclopropoxycarbonyl)ethyl group, 1-methyl-1-(cyclobutoxycarbonyl)ethyl group, 1-methyl-1-(cyclopentyloxycarbonyl)ethyl group and 1-methyl-1-(cyclohexyloxycarbonyl)ethyl group; the (C3–C6 alkenyloxy)carbonyl C1–C3 alkyl group represented by $R^6$ may include allyloxycarbonylmethyl group, 1-methyl-2-propenyloxycarbonylmethyl group, 2-methyl-2-propenyloxycarbonylmethyl group, 1,1-dimethyl-2-propenyloxycarbonylmethyl group, 1-(allyloxycarbonyl)ethyl group, 1-(1-methyl-2-propenyloxycarbonyl)ethyl group, 1-(2-methyl-2-propenyloxycarbonyl)ethyl group, 1-(1,1-dimethyl-2-propenyloxycarbonyl)ethyl group, 1-methyl-1-(allyloxycarbonyl)ethyl group, 1-methyl-1-(1-methyl-2-propenyloxycarbonyl)ethyl group, 1-methyl-1-(2-methyl-2-propenyloxycarbonyl)ethyl group and 1-methyl-1-(1,1-dimethyl-2-propenyloxycarbonyl)ethyl group; the (C3–C6 alkynyloxy)carbonyl C1–C3 alkyl group represented by $R^6$ may include propargyloxycarbonylmethyl group, 1-methyl-2-propynyloxycarbonylmethyl group, 2-butynyloxycarbonylmethyl group, 1,1-dimethyl-2-propynyloxycarbonylmethyl group, 1-(propargyloxycarbonyl)ethyl group, 1-(1-methyl-2-propynyloxycarbonyl)ethyl group, 1-(2-butynyloxycarbonyl)ethyl group, 1-(1,1-dimethyl-2-propynyloxycarbonyl)ethyl group, 1-methyl-1-(propargyloxycarbonyl)ethyl group, 1-methyl-1-(1-methyl-2-propynyloxycarbonyl)ethyl group, 1-methyl-1-(2-butynyloxycarbonyl)ethyl group and 1-methyl-1-(1,1-dimethyl-2-propynyloxycarbonyl)ethyl group; the C1–C3 alkoxy (C1–C3 alkoxy)carbonyl C1–C3 alkyl group represented by $R^6$ may include methoxymethoxycarbonylmethyl group, 2-methoxyethoxycarbonylmethyl group, ethoxymethoxycarbonylmethyl group, 2-ethoxyethoxycarbonylmethyl group, 1-(methoxymethoxycarbonyl)ethyl group, 1-(2-methoxyethoxycarbonyl)ethyl group, 1-(ethoxymethoxycarbonyl)ethyl group, 1-(2-ethoxyethoxycarbonyl)ethyl group, 1-methyl-1-(methoxymethoxycarbonyl)ethyl group, 1-methyl-1-(2-methoxyethoxycarbonyl)ethyl group, 1-methyl-1-(ethoxymethoxycarbonyl)ethyl group and 1-methyl-1-(2-ethoxyethoxycarbonyl)ethyl group; the carboxy (C1–C3 alkoxy)carbonyl C1–C3 alkyl group represented by $R^6$ may include carboxymethoxycarbonylmethyl group, 1-(carboxy)ethoxycarbonylmethyl group, 1-(carboxymethoxycarbonyl)ethyl group, 1-{1-(carboxy)ethoxycarbonyl}ethyl group, 1-methyl-1-(carboxy)ethoxycarbonylmethyl group and 1-{1-methyl-1-(carboxy)ethoxycarbonyl}ethyl group; the (C1–C6 alkoxy)carbonyl (C1–C3 alkoxy)carbonyl C1–C3 alkyl group represented by $R^6$ may include methoxycarbonylmethoxycarbonylmethyl group, 1-(methoxycarbonyl)ethoxycarbonylmethyl group, 1-(methoxycarbonylmethoxycarbonyl)ethyl group, 1-{1-(methoxycarbonyl)ethoxycarbonyl}ethyl group, 1-methyl-(methoxycarbonyl)ethoxycarbonylmethyl group, 1-{1-methyl-1-(methoxycarbonyl)ethoxycarbonyl}ethyl group, ethoxycarbonylmethoxycarbonylmethyl group, 1-(ethoxycarbonyl)ethoxycarbonylmethyl group, 1-(ethoxycarbonylmethoxycarbonyl)ethyl group, 1-{1-(ethoxycarbonyl)ethoxycarbonyl}ethyl group, 1-methyl-1-(ethoxycarbonyl)ethoxycarbonylmethyl group and 1-{1-methyl-1-(ethoxycarbonyl)ethoxycarbonyl}ethyl group; the (C1–C6 haloalkoxy)carbonyl (C1–C3 alkoxy)carbonyl C1–C3 alkyl group represented by $R^6$ may include 2-fluoroethoxycarbonylmethoxycarbonylmethyl group, 1-(2-fluoroethoxycarbonyl)ethoxycarbonylmethyl group, 1-(2 -fluoroethoxycarbonylmethoxycarbonyl)ethyl group, 1-{1-(2-fluoroethoxycarbonyl)ethoxycarbonyl}ethyl group, 1-methyl-1-(2-fluoroethoxycarbonyl)ethoxycarbonylmethyl group, 1-{1-methyl-1-(2-fluoroethoxycarbonyl)ethoxycarbonyl}ethyl group, 2-chloroethoxycarbonylmethoxycarbonylmethyl group, 1-(2-chloroethoxycarbonyl)ethoxycarbonylmethyl group, 1-(2-chloroethoxycarbonylmethoxycarbonyl)ethyl group, 1-{1-(2-chloroethoxycarbonyl)ethoxycarbonyl}ethyl group, 1-methyl-1-(2-chloroethoxycarbonyl) ethoxycarbonylmethyl group and 1-{methyl-1-(2-chloroethoxycarbonyl)ethoxycarbonyl}ethyl group; the (C3–C6 alkenyloxy)carbonyl (C1–C3 alkoxy)carbonyl C1–C3 alkyl group represented by $R^6$ may include allyloxycarbonylmethoxycarbonylmethyl group, 1-(allyloxycarbonyl)ethoxycarbonylmethyl group, 1-(allyloxycarbonylmethoxycarbonyl)ethyl group, 1-{1-(allyloxycarbonyl)ethoxycarbonyl}ethyl group, 1-methyl-1-(allyloxycarbonyl)ethoxycarbonylmethyl group and 1-{1-methyl-1-(allyloxycarbonyl)ethoxycarbonyl}ethyl group; the (C3–C6 alkynyloxy)carbonyl (C1–C3 alkoxy)carbonyl C1–C3 alkyl group represented by $R^6$ may include propargyloxycarbonylmethoxycarbonylmethyl group, 1-(propargyloxycarbonyl)ethoxycarbonylmethyl group, 1-(propargyloxycarbonylmethoxycarbonyl)ethyl group, 1-{1-(propargyloxycarbonyl)ethoxycarbonyl}ethyl group, 1-methyl-1-(propargyloxycarbonyl)ethoxycarbonylmethyl group and 1-{1-methyl-1-(propargyloxycarbonyl) ethoxycarbonyl}ethyl group; the (C3–C8 cycloalkoxy) carbonyl (C1–C3 alkoxy)carbonyl C1–C3 alkyl group represented by $R^6$ may include cyclopentyloxycarbonylmethoxycarbonylmethyl group, 1-(cyclopentyloxycarbonyl)ethoxycarbonylmethyl group, 1-(cyclopentyloxycarbonylmethoxycarbonyl)ethyl group, 1-{1-(cyclopentyloxycarbonyl)ethoxycarbonyl}ethyl group, 1-methyl-1-(cyclopentyloxycarbonyl) ethoxycarbonylmethyl group and 1-{1-methyl-1-(cyclopentyloxycarbonyl)ethoxycarbonyl}ethyl group; the optionally substituted aryloxycarbony C1–C3 alkyl group represented by $R^6$ may include phenoxycarbonylmethyl group, 1-phenoxycarbonylethyl group and 1-methyl-1-(phenoxycarbonyl)ethyl group; the optionally substituted aryl (C1–C3 alkoxy)carbony C1–C3 alkyl group represented by $R^6$ may include benzyloxycarbonylmethyl group, 1-benzyloxycarbonylethyl group, 1-methyl-1-(benzyloxycarbonyl)ethyl group, phenethyloxycarbonylmethyl group, 1-phenethyloxycarbonylethyl group and 1-methyl-1-(phenethyloxycarbonyl)ethyl group; and the (C1–C6 alkoxy)carbony group represented by $R^6$ may include methoxycarbonyl group, ethoxycarbonyl group, propoxycarbonyl group and isopropoxycarbonyl group. The C1–C6 alkyl group represented by $R^7$ may include methyl group, ethyl group, propyl group, isopropyl group, butyl group, isobutyl group, sec-butyl group, tert-butyl group, pentyl group and hexyl group; the C1–C6 haloalkyl group represented by $R^7$ may include trifluoromethyl group, difluoromethyl group, 2-fluoroethyl group, 2-chloroethyl group and 2-bromoethyl group; the C3–C8 cycloalkyl group represented by $R^7$ may include cyclopropyl group, cyclobutyl group, cyclopentyl group and cyclohexyl group; the C1–C6 alkoxy group represented by $R^7$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^7$ may include 2-fluoroethoxy group, 2-chloroethoxy group and 2-bromoethoxy group; the C3–C8 cycloalkoxy group represented by $R^7$ may include cyclopropoxy group, cyclobutoxy group, cyclopentyloxy group and cyclohexyloxy group; the C3–C6 alkenyloxy group represented by $R^7$ may include allyloxy group, 1-methyl-2-propynyloxy group, 2-methyl-2-propenyloxy group and 1,1-dimethyl-2-propenyloxy group;

the C3–C6 alkynyloxy group represented by $R^7$ may include propargyloxy group, 1-methyl-2-propynyloxy group, 2-butynyloxy group and 1,1-dimethyl-2-propynyloxy group; the (C1–C3 alkoxy) C1–C3 alkoxy group represented by $R^7$ may include methoxymethoxy group, 2-methoxyethoxy group, ethoxymethoxy group and so on; the carboxy C1–C3 alkoxy group represented by $R^7$ may include carboxymethoxy group, 1-carboxyethoxy group and 1-methyl-1-(carboxy)ethoxy group; the (C1–C6 alkoxy)carbonyl C1–C3 alkoxy group represented by $R^7$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl) ethoxy group, 1-(isopropoxycarbonyl)ethoxy group, 1-(butoxycarbonyl)ethoxy group, 1-(isobutoxycarbonyl) ethoxy group, 1-(sec-butoxycarbonyl)ethoxy group, 1-(tert-butoxycarbonyl)ethoxy group, 1-(pentyloxycarbonyl) ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^7$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^7$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl) ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; the (C3–C6 alkynyloxy)carbonyl C1–C3 alkoxy group represented by $R^7$ may include propargyloxycarbonylmethoxy group, 1-methyl-2-propynyloxycarbonylmethoxy group, 2-butynyloxycarbonylmethoxy group, 1,1-dimethyl-2- propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group; the optionally substituted phenoxy group represented by $R^7$ may include phenoxy group; and the optionally substituted benzyloxy group represented by $R^7$ may include benzyloxy group. The C1–C6 alkoxy group represented by $R^8$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^8$ may include 2-fluoroethoxy group, 2-chloroethoxy group, 2-bromoethoxy group and so on; the C3–C8 cycloalkoxy group represented by $R^8$ may include cyclopropoxy group, cyclobutoxy group, cyclopentyloxy group and cyclohexyloxy group; the C3–C6 alkenyloxy group represented by $R^8$ may include allyloxy group, 1-methyl-2-propenyloxy group, 2-methyl-2-propenyloxy group and 1,1-dimethyl-2-propenyloxy group; the C3–C6 alkynyloxy group represented by $R^8$ may include propargyloxy group, 1-methyl-2-propynyloxy group, 2-butynyloxy group and 1,1-dimethyl-2-propynyloxy group; the (C1–C3 alkoxy) C1–C3 alkoxy group represented by $R^8$ may include methoxymethoxy group, 2-methoxyethoxy group and ethoxymethoxy group; the optionally substituted phenoxy group represented by $R^8$ may include phenoxy group; and the optionally substituted benzyloxy group represented by $R^8$ may include benzyloxy group. The halogen atom represented by $R^9$ may include chlorine atom and bromine atom. The C1–C6 alkoxy group represented by $R^{10}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{10}$ may include 2-fluoroethoxy group, 2-chloroethoxy group and 2-bromoethoxy group; the C3–C8 cycloalkoxy group represented by $R^{10}$ may include cyclopropoxy group, cyclobutoxy group, cyclopentyloxy group and cyclohexyloxy group; the C3–C6 alkenyloxy group represented by $R^{10}$ may include allyloxy group, 1-methyl-2-propenyloxy group, 2-methyl-2-propenyloxy group and 1,1-dimethyl-2-propenyloxy group; the C3–C6 alkynyloxy group represented by $R^{10}$ may include propargyloxy group, 1-methyl-2-propynyloxy group, 2-butynyloxy group and 1,1-dimethyl-2-propynyloxy group; the (C1–C3 alkoxy) C1–C3 alkoxy group represented by $R^{10}$ may include methoxymethoxy group, 2-methoxyethoxy group and ethoxymethoxy group; the optionally substituted phenoxy group represented by $R^{10}$ may include phenoxy group; and the optionally substituted benzyloxy group represented by $R^{10}$ may include benzyloxy group. The halogen atom represented by $R^{11}$ may include chlorine atom and bromine atom. The C1–C6 alkyl group represented by $R^{12}$ may include methyl group, ethyl group and isopropyl group; the C1–C6 haloalkyl group represented by $R^{12}$ may include chloromethyl group, bromomethyl group, fluoromethyl group, dichloromethyl group, dibromomethyl group and difluoromethyl group; the hydroxy C1–C3 alkyl group represented by $R^{12}$ may include hydroxymethyl group and 2-hydroxyethyl group; the (C1–C3 alkoxy) C1–C3 alkyl group represented by $R^{12}$ may include methoxymethyl group, ethoxymethyl group and isopropoxymethyl group; the (C1–C6 alkyl)carbonyloxy C1–C3 alkyl group represented by $R^{12}$ may include methylcarbonyloxymethyl group and ethylcarbonyloxymethyl group; the (C1–C6 haloalkyl)carbonyloxy C1–C3 alkyl group represented by $R^{12}$ may include trifluoroacetoxymethyl group and difluoroacetoxymethyl group; the (C1–C6 alkoxy)carbonyl group represented by $R^{12}$ may include methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group and hexyloxycarbonyl group; the (C1–C6 haloalkoxy)carbonyl group represented by $R^{12}$ may include 2,2,2-trifluoroethoxycarbonyl group, 2-fluoroethoxycarbonyl group, 2-chloroethoxycarbonyl group and 2-bromoethoxycarbonyl group; the (C3–C8 cycloalkoxy)carbonyl group represented by $R^{12}$ may include cyclopropoxycarbonyl group, cyclobutoxycarbonyl group, cyclopentyloxycarbonyl group and cyclohexyloxycarbonyl group; the (C3–C6 alkenyloxy)carbonyl group represented by $R^{12}$ may include allyloxycarbonyl group; the (C3–C6 alkynyloxy)carbonyl group represented by $R^{12}$ may include propargyloxycarbonyl group; and the C1–C3 alkoxy (C1–C3 alkoxy)carbonyl group represented by $R^{12}$ may include methoxymethoxycarbonyl group, 2-methoxyethoxycarbonyl group and 2-ethoxyethoxycarbonyl group. The C1–C3 alkyl group represented by $R^{13}$ may include methyl group and ethyl group. The C1–C6 alkyl group represented by $R^{14}$ may include methyl group, ethyl group and isopropyl group; the C1–C6 haloalkyl group represented by $R^{14}$ may include chloromethyl group, bromomethyl group, fluoromethyl group, dichloromethyl group, dibromomethyl group and difluoromethyl group; the hydroxy C1–C3 alkyl group represented by $R^{14}$ may include hydroxymethyl group and 2-hydroxyethyl group; the (C1–C3 alkoxy) C1–C3 alkyl group represented by $R^{14}$ may include methoxymethyl group, ethoxymethyl group and isopropoxymethyl group; the (C1–C6 alkyl)carbonyloxy C1–C3 alkyl group represented by $R^{14}$ may include acetoxymethyl group and propionyloxymethyl group; the (C1–C6 haloalkyl)carbonyloxy C1–C3 alkyl group represented by $R^{14}$ may include trifluoroacetoxymethyl group and difluoroacetoxymethyl group; the (C1–C6 alkoxy)carbonyl group represented by $R^{14}$ may include methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group and hexyloxycarbonyl group; the (C1–C6 haloalkoxy) carbonyl group represented by $R^{14}$ may include 2,2,2-trifluoroethoxycarbonyl group, 2-fluoroethoxycarbonyl group, 2-chloroethoxycarbonyl group and 2-bromoethoxycarbonyl group; the (C3–C8 cycloalkoxy) carbonyl group represented by $R^{14}$ may include cyclopropoxycarbonyl group, cyclobutoxycarbonyl group, cyclopentyloxycarbonyl group and cyclohexyloxycarbonyl group; the (C3–C6 alkenyloxy)carbonyl group represented by $R^{14}$ may include allyloxycarbonyl group; the (C3–C6 alkynyloxy)carbonyl group represented by $R^{14}$ may include propargyloxycarbonyl group; and the C1–C3 alkoxy (C1–C3 alkoxy)carbonyl group represented by $R^{14}$ may include methoxymethoxycarbonyl group, 2-methoxyethoxycarbonyl group and 2-ethoxyethoxycarbonyl group. The C1–C6 alkyl group represented by $R^{15}$ may include methyl group, ethyl group, propyl group, isopropyl group, butyl group, isobutyl group, sec-butyl group, tert-butyl group, pentyl group and hexyl group; the C1–C6 haloalkyl group represented by $R^{15}$ may include trifluoromethyl group, difluoromethyl group, 2-fluoroethyl group, 2-chloroethyl group and 2-bromoethyl group; the C3–C8 cycloalkyl group represented by $R^{15}$ may include cyclopropyl group, cyclobutyl group, cyclopentyl group and cyclohexyl group; the (C3–C8 cycloalkyl) C1–C3 alkyl group represented by $R^{15}$ may include cyclopropylmethyl group, cyclobutylmethyl group, cyclopentylmethyl group and cyclohexylmethyl group; the C3–C6 alkenyl group represented by $R^{15}$ may include allyl group, 1-methyl-2-propenyl group, 2-methyl-2-propenyl group and 1,1-dimethyl-2-propenyl group; the C3–C6 alkynyl group represented by $R^{15}$ may include propargyl group, 1-methyl-2-propynyl group, 2-butynyl group and 1,1-dimethyl-2-propynyl group; the cyano C1–C3 alkyl group represented by $R^{15}$ may include cyanomethyl group, 1-cyanoethyl group, 2-cyanoethyl group and 1-methyl-2-cyanoethyl group; the (C1–C3 alkoxy) C1–C3 alkyl group represented by $R^{15}$ may include methoxymethyl group, 2-methoxyethyl group, ethoxymethyl group and 2-ethoxyethyl group; the (C1–C3 alkylthio) C1–C3 alkyl group represented by $R^{15}$ may include methylthiomethyl group, 2-ethylthioethyl group and 2-methylthioethyl group; the (C1–C6 alkyl) carbonyl group represented by $R^{15}$ may include acetyl group, propionyl group, butyryl group, isobutyryl group and pivaloyl group; the (C1–C6 haloalkyl)carbonyl group represented by $R^{15}$ may include trifluoroacetyl group, difluoroacetyl group, trichloroacetyl group and dichloroacetyl group; the (C3–C8 cycloalkyl)carbonyl group represented by $R^{15}$ may include cyclopropylcarbonyl group, cyclopentylcarbonyl group and cyclohexylcarbonyl group; the carboxy C1–C3 alkyl group represented by $R^{15}$ may include carboxymethyl group, 1-carboxyethyl group, 1-methyl-1-carboxyethyl group, 1-carboxypropyl group, 2-carboxyethyl group and 1-methyl-2-carboxyethyl group; the (C1–C6 alkoxy)carbonyl C1–C3 alkyl group represented by $R^{15}$ may include methoxycarbonylmethyl group, ethoxycarbonylmethyl group, propoxycarbonylmethyl group, isopropoxycarbonylmethyl group, butoxycarbonylmethyl group, isobutoxycarbonylmethyl group, sec-butoxycarbonylmethyl group, tert-butoxycarbonylmethyl group, pentyloxycarbonylmethyl group, isopentyloxycarbonylmethyl group, hexyloxycarbonylmethyl group, isohexyloxycarbonylmethyl group, 1-methoxycarbonylethyl group, 1-ethoxycarbonylethyl group, 1-(propoxycarbonyl)ethyl group, 1-(isopropoxycarbonyl)ethyl group, 1-(butoxycarbonyl)ethyl group, 1-(isobutoxycarbonyl)ethyl group, 1-(sec-butoxycarbonyl)ethyl group, 1-(tert-butoxycarbonyl)ethyl group, 1-(pentyloxycarbonyl)ethyl group, 1-(isopentyloxycarbonyl)ethyl group, 1-(hexyloxycarbonyl)ethyl group, 1-(isohexyloxycarbonyl) ethyl group, 1-methyl-1-(methoxycarbonyl)ethyl group, 1-methyl-1-(ethoxycarbonyl)ethyl group, 1-methyl-1-(isopropoxycarbonyl)ethyl group, 1-methyl-1-(isopropoxycarbonyl)ethyl group, 1-methyl-1-(butoxycarbonyl)ethyl group, 1-methyl-1-(isobutoxycarbonyl)ethyl group, 1-methyl-1-(sec-butoxycarbonyl)ethyl group, 1-methyl-1-(tert-butoxycarbonyl)ethyl group, 1-methyl-1-(pentyloxycarbonyl)ethyl group, 1-methyl-1-(isopentyloxycarbonyl)ethyl group, 1-methyl-1-(hexyloxycarbonyl)ethyl group and 1-methyl-1-(isohexyloxycarbonyl)ethyl group; the (C1–C6 haloalkoxy) carbonyl C1–C3 alkyl group represented by $R^{15}$ may include 2-fluoroethoxycarbonylmethyl group, 2-chloroethoxycarbonylmethyl group, 2-bromoethoxycarbonylmethyl group, 2,2,2-trifluoroethoxycarbonylmethyl group, 1-(2-fluoroethoxycarbonyl)ethyl group, 1-(2-chloroethoxycarbonyl)ethyl group, 1-(2-bromoethoxycarbonyl)ethyl group, 1-(2,2,2-trifluoroethoxycarbonyl)ethyl group, 1-methyl-1-(2-fluoroethoxycarbonyl)ethyl group, 1-methyl-1-(2-chloroethoxycarbonyl)ethyl group, 1-methyl-1-(2-bromoethoxycarbonyl)ethyl group and 1-methyl-1-(2,2,2-trifluoroethoxycarbonyl)ethyl group; the (C3–C8 cycloalkoxy)carbonyl C1–C3 alkyl group represented by $R^{15}$ may include cyclopropoxycarbonylmethyl group, cyclobutoxycarbonylmethyl group, cyclopentyloxycarbonylmethyl group, cyclohexyloxycarbonylmethyl group, 1-cyclopropoxycarbonylethyl group, 1-cyclobutoxycarbonylethyl group, 1-cyclopentyloxycarbonylethyl group, 1-cyclohexyloxycarbonylethyl group, 1-methyl-(1-cyclopropoxycarbonyl)ethyl group, 1-methyl-(1-cyclobutoxycarbonyl)ethyl group, 1-methyl-(1-cyclopentyloxycarbonyl)ethyl group and 1-methyl-(1-cyclohexyloxycarbonyl)ethyl group; the (C3–C6 alkenyloxy)carbonyl C1–C3 alkyl group represented by $R^{15}$ may include allyloxycarbonylmethyl group, (1-methyl-2-propenyloxy)carbonylmethyl group, 2-methyl-2-propenyloxycarbonylmethyl group, 1,1-dimethyl-2-propenyloxycarbonylmethyl group, 1-(allyloxycarbonyl)ethyl group, 1-(1-methyl-2-propenyloxycarbonyl)ethyl group, 1-(2-methyl-2-propenyloxycarbonyl) ethyl group, 1-(1,1-dimethyl-2-propenyloxycarbonyl)ethyl group, 1-methyl-1-(allyloxycarbonyl)ethyl group, 1-methyl-1-((-methyl-2-propenyloxycarbonyl)ethyl group, 1-methyl-1-(2-methyl-2-propenyloxycarbonyl)ethyl group and 1-methyl-1-(1,1-dimethyl-2-propenyloxycarbonyl)ethyl group; the (C3–C6 alkynyloxy)carbonyl C1–C3 alkyl group represented by $R^{15}$ may include propargyloxycarbonylmethyl group, 1-methyl-2-propynyloxycarbonylmethyl group, 2-butynyloxycarbonylmethyl group, 1,1-dimethyl-2-propynyloxycarbonylmethyl group, 1-(propargyloxycarbonyl)ethyl group, 1-(1-methyl-2-propynyloxycarbonyl)ethyl group, 1-(2-butynyloxycarbonyl)ethyl group, 1-(1,1-dimethyl-2-propynyloxycarbonyl)ethyl group, 1-methyl-1-(propargyloxycarbonyl)ethyl group, 1-methyl-1-(1-methyl-2-propynyloxycarbonyl)ethyl group, 1-methyl-1-(2-butynyloxycarbonyl)ethyl group and 1-methyl-1-(1,1-dimethyl-2-propynyloxycarbonyl)ethyl group; the C1–C3 alkoxy (C1–C3 alkoxy)carbonyl C1–C3 alkyl group represented by $R^{15}$ may include methoxymethoxycarbonylmethyl group, 2-methoxyethoxycarbonylmethyl group, ethoxymethoxycarbonylmethyl group, 2-ethoxyethoxycarbonylmethyl group, 1-(methoxymethoxycarbonyl)ethyl group, 1-(2-methoxyethoxycarbonyl)ethyl group, 1-(ethoxymethoxycarbonyl)ethyl group, 1-(2-ethoxyethoxycarbonyl)ethyl group, 1-methyl-1-(methoxymethoxycarbonyl)ethyl group, 1-methyl-1-(2-methoxyethoxycarbonyl)ethyl group, 1-methyl-1-(ethoxymethoxycarbonyl)ethyl group and 1-methyl-1-(2-ethoxyethoxycarbonyl)ethyl group; the carboxy (C1–C3 alkoxy)carbonyl C1–C3 alkyl group represented by $R^{15}$ may include carboxymethoxycarbonylmethyl group, 1-(carboxy)ethoxycarbonylmethyl group, 1-(carboxymethoxycarbonyl) ethyl group, 1-{1-(carboxy)ethoxycarbonyl}ethyl group, {1-methyl-1-(carboxy)ethoxy}carbonylmethyl group and 1-{1-methyl-1-(carboxy)ethoxycarbonyl}ethyl group; the (C1–C6 alkoxy)carbonyl (C1–C3 alkoxy)carbonyl C1–C3 alkyl group represented by $R^{15}$ may include methoxycarbonylmethoxycarbonylmethyl group, 1-(methoxycarbonyl)

ethoxycarbonylmethyl group, 1-(methoxycarbonylmethoxycarbonyl)ethyl group, 1-{1-(methoxycarbonyl)ethoxycarbonyl}ethyl group, 1-methyl-1-(methoxycarbonyl)ethoxycarbonylmethyl group, 1-{1-methyl-1-(methoxycarbonyl)ethoxycarbonyl}ethyl group, ethoxycarbonylmethoxycarbonylmethyl group, 1-(ethoxycarbonyl)ethoxycarbonylmethyl group, 1-(ethoxycarbonylmethoxycarbonyl)ethyl group, 1-{1-(ethoxycarbonyl)ethoxycarbonyl}ethyl group, 1-{1-methyl-1-(ethoxycarbonyl)ethoxycarbonyl}ethyl group and 1-{1-methyl-1-(ethoxycarbonyl)ethoxycarbonyl}ethyl group; the (C1–C6 haloalkoxy)carbonyl (C1–C3 alkoxy)carbonyl C1–C3 alkyl group represented by $R^{15}$ may include 2-fluoroethoxycarbonylmethoxycarbonylmethyl group, 1-(2-fluoroethoxycarbonyl)ethoxycarbonylmethyl group, 1-(2-fluoroethoxycarbonylmethoxycarbonyl)ethyl group, 1-{1-(2-fluoroethoxycarbonyl)ethoxycarbonyl}ethyl group, 1-methyl-=-(2-fluoroethoxycarbonyl)ethoxycarbonylmethyl group, 1-{1-methyl-1-(2-fluoroethoxycarbonyl)ethoxycarbonyl}ethyl group, 2-chloroethoxycarbonylmethoxycarbonylmethyl group, 1-(2-chloroethoxycarbonyl)ethoxycarbonylmethyl group, 1-(2-chloroethoxycarbonylmethoxycarbonyl)ethyl group, 1-{1-(2-chloroethoxycarbonyl)ethoxycarbonyl}ethyl group, 1-methyl-2-(2-chloroethoxycarbonyl)ethoxycarbonylmethyl group and 1-{1-methyl-1-(2-chloroethoxycarbonyl)ethoxycarbonyl}ethyl group; the (C3–C8 cycloalkoxy)carbonyl (C1–C3 alkoxy)carbonyl C1–C3 alkyl group represented by $R^{15}$ may include cyclopentyloxycarbonylmethoxycarbonylmethyl group, 1-(cyclopentyloxycarbonyl)ethoxycarbonylmethyl group, 1-(cyclopentyloxycarbonylmethoxycarbonyl)ethyl group, 1-{1-(cyclopentyloxycarbonyl)ethoxycarbonyl}ethyl group, 1-methyl-1-(cyclopentyloxycarbonyl)ethoxycarbonylmethyl group and 1-{1-methyl-1-(cyclopentyloxycarbonyl)ethoxycarbonyl}ethyl group; the (C3–C6 alkenyloxy)carbonyl (C1–C3 alkoxy)carbonyl C1–C3 alkyl group represented by $R^{15}$ may include allyloxycarbonylmethoxycarbonylmethyl group, 1-(allyloxycarbonyl)ethoxycarbonylmethyl group, 1-(allyloxycarbonylmethoxycarbonyl)ethyl group, 1-{1-(allyloxycarbonyl)ethoxycarbonyl}ethyl group, 1-methyl-1-(allyloxycarbonyl)ethoxycarbonylmethyl group and 1-{1-methyl-1-(allyloxycarbonyl)ethoxycarbonyl}ethyl group; the (C3–C6 alkynyloxy)carbonyl (C1–C3 alkoxy)carbonyl C1–C3 alkyl group represented by $R^{15}$ may include propargyloxycarbonylmethoxycarbonylmethyl group, 1-(propargyloxycarbonyl)ethoxycarbonylmethyl group, 1-(propargyloxycarbonylmethoxycarbonyl)ethyl group, 1-{1-(propargyloxycarbonyl)ethoxycarbonyl}ethyl group, 1-methyl-1-(propargyloxycarbonyl)ethoxycarbonylmethyl group and 1-{1-methyl-1-(propargyloxycarbonyl)ethoxycarbonyl}ethyl group; the optionally substituted aryloxycarbonyl C1–C3 alkyl group represented by $R^{15}$ may include phenoxycarbonylmethyl group, 1-phenoxycarbonylethyl group and 1-methyl-1-(phenoxycarbonyl)ethyl group; the optionally substituted aryl (C1–C3 alkoxy)carbonyl C1–C3 alkyl group represented by $R^{15}$ may include benzyloxycarbonylmethyl group, 1-benzyloxycarbonylethyl group, 1-methyl-1-(benzyloxycarbonyl)ethyl group, phenethyloxycarbonylmethyl group, 1-phenethyloxycarbonylethyl group and 1-methyl-1-(phenethyloxycarbonyl)ethyl group; and the (C1–C6 alkoxy)carbonyl group represented by $R^{15}$ may include methoxycarbonyl group, ethoxycarbonyl group, propoxycarbonyl group and isopropoxycarbonyl group. The C1–C3 alkyl group represented by $R^{17}$ may include methyl group, ethyl group, propyl group and isopropyl group; and the C1–C3 haloalkyl group represented by $R^{17}$ may include chloromethyl group and trifluoromethyl group. The C1–C3 alkyl group represented by $R^{18}$ may include methyl group and ethyl group; and the (C1–C6 alkoxy)carbonyl group represented by $R^{18}$ may include methoxycarbonyl group and ethoxycarbonyl group. The halogen atom represented by $R^{19}$ may include fluorine atom, chlorine atom, bromine atom and iodine atom. The C1–C6 alkyl group represented by $R^{19}$ may include methyl group, ethyl group, propyl group, isopropyl group, butyl group, isobutyl group, sec-butyl group, tert-butyl group, pentyl group and hexyl group; the C1–C6 haloalkyl group represented by $R^{19}$ may include trifluoromethyl group, difluoromethyl group, 2-fluoroethyl group, 2-chloroethyl group and 2-bromoethyl group; the C1–C6 alkoxy group represented by $R^{19}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{19}$ may include 2-fluoroethoxy group, 2-chloroethoxy group and 2-bromoethoxy group; the C3–C8 cycloalkoxy group represented by $R^{19}$ may include cyclopropoxy group, cyclobutoxy group, cyclopentyloxy group and cyclohexyloxy group; the C3–C6 alkenyloxy group represented by $R^{19}$ may include allyloxy group, 1-methyl-2-propenyloxy group, 2-methyl-2-propenyloxy group and 1,1-dimethyl-2-propenyloxy group; the C3–C6 alkynyloxy group represented by $R^{19}$ may include propargyloxy group, 1-methyl-2-propynyloxy group, 2-butynyloxy group and 1,1-dimethyl-2-propynyloxy group; the carboxy C1–C3 alkoxy group represented by $R^{19}$ may include carboxymethoxy group, 1-carboxyethoxy group and 1-methyl-1-(carboxy)ethoxy group; the (C1–C6 alkoxy)carbonyl C1–C3 alkoxy group represented by $R^{19}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl)ethoxy group, 1-(isobutoxycarbonyl)ethoxy group, 1-(sec-butoxycarbonyl)ethoxy group, 1-(tert-butoxycarbonyl)ethoxy group, 1-(ethoxycarbonyl)ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{19}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{19}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{19}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2 -propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group. The halogen atom represented by $R^{20}$ may include fluorine atom, chlorine atom, bromine atom and iodine atom; the C1–C6 alkyl group represented by $R^{20}$ may include methyl group, ethyl group, propyl group, isopropyl group, butyl group, isobutyl group, sec-butyl group, tert-butyl group, pentyl group and hexyl group; the C1–C6 haloalkyl group represented by $R^{20}$ may include trifluoromethyl group, difluoromethyl group, 2-fluoroethyl group, 2-chloroethyl group and 2-bromoethyl group; the C1–C6 alkoxy group represented by $R^{20}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{20}$ may include 2-fluoroethoxy group, 2-chloroethoxy group and 2-bromoethoxy group; the C3–C8 cycloalkoxy group represented by $R^{20}$ may include cyclopropoxy group, cyclobutoxy group, cyclopentyloxy group and cyclohexyloxy group; the C3–C6 alkenyloxy group represented by $R^{20}$ may include allyloxy group, 1-methyl-2-propenyloxy group, 2-methyl-2-propenyloxy group and 1,1-dimethyl-2-propenyloxy group; the C3–C6 alkynyloxy group represented by $R^{20}$ may include propargyloxy group, 1-methyl-2-propynyloxy group, 2-butynyloxy group and 1,1-dimethyl-2-propynyloxy group; the carboxy C1–C3 alkoxy group represented by $R^{20}$ may include carboxymethoxy group, 1-carboxyethoxy group and 1-methyl-1-(carboxy)ethoxy group; the (C1–C6 alkoxy)carbonyl C1–C3 alkoxy group represented by $R^{20}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl)ethoxy group, 1-(isobutoxycarbonyl)ethoxy group, 1-(sec-butoxycarbonyl)ethoxy group, 1-(tert-butoxycarbonyl)ethoxy group, 1-(pentyloxycarbonyl)ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl) ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{20}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-(1-cyclopropoxycarbonyl)ethoxy group, 1-methyl-(1-cyclobutoxycarbonyl)ethoxy group, 1-methyl-(1-cyclopentyloxycarbonyl)ethoxy group and 1-methyl-(1-cyclohexyloxycarbonyl)ethoxy group; the (C3–C6 alkenyloxy)carbonyl C1–C3 alkoxy group represented by $R^{20}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{20}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group. The C1–C3 alkyl group represented by $R^{21}$ and $R^{22}$ may include methyl group, ethyl group and propyl group; the C2–C5 alkylene group represented by $R^{21}$ and $R^{22}$ may include ethylene group, trimethylene group, tetramethylene group and pentamethylene group; and the C1–C3 alkyleneoxy C1–C3 alkylene group represented by $R^{21}$ and $R^{22}$ may include ethyleneoxyethylene group. The C1–C3 alkyl group represented by $R^{23}$ and $R^{24}$ may include methyl group, ethyl group and propyl group; the C2–C5 alkylene group represented by $R^{23}$ and $R^{24}$ may include ethylene group, trimethylene group, tetramethylene group and pentamethylene group; and the (C1–C3 alkyleneoxy) C1–C3 alkylene group represented by $R^{23}$ and $R^{24}$ may include ethyleneoxyethylene group. The C1–C3 alkyl group represented by $R^{25}$ may include methyl group and ethyl group; and the (C1–C6 alkoxy)carbonyl group represented by $R^{25}$ may include methoxycarbonyl group and ethoxycarbonyl group. The halogen atom represented by $R^{26}$ may include fluorine atom, chlorine atom, bromine atom and iodine atom; the C1–C6 alkyl group represented by $R^{26}$ may include methyl group, ethyl group, propyl group, isopropyl group, butyl group, isobutyl group, sec-butyl group, tert-butyl group, pentyl group and hexyl group; the C1–C6 haloalkyl group represented by $R^{26}$ may include trifluoromethyl group, difluoromethyl group, 2-fluoroethyl group, 2-chloroethyl group and 2-bromoethyl group; the C1–C6 alkoxy group represented by $R^{26}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{26}$ may include 2-fluoroethoxy group, 2-chloroethoxy group and 2-bromoethoxy group; the C3–C8 cycloalkoxy group represented by $R^{26}$ may include cyclopropoxy group, cyclobutoxy group, cyclopentyloxy group and cyclohexyloxy group; the C3–C6 alkenyloxy group represented by $R^{26}$ may include allyloxy group, 1-methyl-2-propenyloxy group, 2-methyl-2-propenyloxy group and 1,1-dimethyl-2-propenyloxy group; the C3–C6 alkynyloxy group represented by $R^{26}$ may include propargyloxy group, 1-methyl-2-propynyloxy group, 2-butynyloxy group and 1,1-dimethyl-2-propynyloxy group; the carboxy C1–C3 alkoxy group represented by $R^{26}$ may include carboxymethoxy group, 1-carboxyethoxy group and 1-methyl-1-(carboxy)ethoxy group; the (C1–C6 alkoxy)carbonyl C1–C3 alkoxy group represented by $R^{26}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl)ethoxy group, 1-(isobutoxycarbonyl)ethoxy group, 1-(sec-butoxycarbonyl)ethoxy group, 1-(tert-butoxycarbonyl)ethoxy group, 1-(pentyloxycarbonyl)ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{26}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{26}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{26}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl) ethoxy group and 1-methyl-1-(1,1-dimethyl-2 -propynyloxycarbonyl)ethoxy group. The halogen atom represented by $R^{27}$ may include fluorine atom, chlorine atom, bromine atom and iodine atom; the C1–C6 alkyl group represented by $R^{27}$ may include methyl group, ethyl group, propyl group, isopropyl group, butyl group, isobutyl group, sec-butyl group, tert-butyl group, pentyl group and hexyl group; the C1–C6 haloalkyl group represented by $R^{27}$ may include trifluoromethyl group, difluoromethyl group, 2-fluoroethyl group, 2-chloroethyl group and 2-bromoethyl group; the C1–C6 alkoxy group represented by $R^{27}$ may include methoxy group, ethoxy group, propoxy group, isopropoxy group, butoxy group, isobutoxy group, sec-butoxy group, tert-butoxy group, pentyloxy group and hexyloxy group; the C1–C6 haloalkoxy group represented by $R^{27}$ may include 2-fluoroethoxy group, 2-chloroethoxy group and 2-bromoethoxy group; the C3–C8 cycloalkoxy group represented by $R^{27}$ may include cyclopropoxy group, cyclobutoxy group, cyclopentyloxy group and cyclohexyloxy group; the C3–C6 alkenyloxy group represented by $R^{27}$ may include allyloxy group, 1-methyl-2-propenyloxy group, 2-methyl-2-propenyloxy group and 1,1-dimethyl-2-propenyloxy group; the C3–C6 alkynyloxy group represented by $R^{27}$ may include propargyloxy group, 1-methyl-2-propynyloxy group, 2-butynyloxy group and 1,1-dimethyl-2-propynyloxy group; the carboxy C1–C3 alkoxy group represented by $R^{27}$ may include carboxymethoxy group, 1-carboxyethoxy group and 1-methyl-1-(carboxy)ethoxy group; the (C1–C6 alkoxy)carbonyl C1–C3 alkoxy group represented by $R^{27}$ may include methoxycarbonylmethoxy group, ethoxycarbonylmethoxy group, propoxycarbonylmethoxy group, isopropoxycarbonylmethoxy group, butoxycarbonylmethoxy group, isobutoxycarbonylmethoxy group, sec-butoxycarbonylmethoxy group, tert-butoxycarbonylmethoxy group, pentyloxycarbonylmethoxy group, isopentyloxycarbonylmethoxy group, hexyloxycarbonylmethoxy group, isohexyloxycarbonylmethoxy group, 1-methoxycarbonylethoxy group, 1-ethoxycarbonylethoxy group, 1-(propoxycarbonyl)ethoxy group, 1-(isopropoxycarbonyl)ethoxy group, 1-(butoxycarbonyl)ethoxy group, 1-(isobutoxycarbonyl)ethoxy group, 1-(sec-butoxycarbonyl)ethoxy group, 1-(tert-butoxycarbonyl)ethoxy group, 1-(pentyloxycarbonyl)ethoxy group, 1-(isopentyloxycarbonyl)ethoxy group, 1-(hexyloxycarbonyl)ethoxy group, 1-(isohexyloxycarbonyl)ethoxy group, 1-methyl-1-(methoxycarbonyl)ethoxy group, 1-methyl-1-(ethoxycarbonyl)ethoxy group, 1-methyl-1-(propoxycarbonyl)ethoxy group, 1-methyl-1-(isopropoxycarbonyl)ethoxy group, 1-methyl-1-(butoxycarbonyl)ethoxy group, 1-methyl-1-(isobutoxycarbonyl)ethoxy group, 1-methyl-1-(sec-butoxycarbonyl)ethoxy group, 1-methyl-1-(tert-butoxycarbonyl)ethoxy group, 1-methyl-1-(pentyloxycarbonyl)ethoxy group, 1-methyl-1-(isopentyloxycarbonyl)ethoxy group, 1-methyl-1-(hexyloxycarbonyl)ethoxy group and 1-methyl-1-(isohexyloxycarbonyl)ethoxy group; the (C3–C8 cycloalkoxy)carbonyl C1–C3 alkoxy group represented by $R^{27}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{27}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; and the (C3–C6 alkynyloxy)carbonyl C1–C3 alkoxy group represented by $R^{27}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group. The C1–C6 alkyl group represented by $R^{28}$, $R^{29}$, $R^{30}$ and $R^{31}$ may include methyl group and ethyl group. The halogen atom represented by $R^{32}$, $R^{33}$ and $R^{34}$ may include fluorine atom, chlorine atom, bromine atom and iodine atom; the C1–C3 alkyl group represented by $R^{32}$, $R^{33}$ and $R^{34}$ may include methyl group, ethyl group, propyl group and isopropyl group; the C1–C3 haloalkyl group represented by $R^{32}$, $R^{33}$ and $R^{34}$ may include trifluoromethyl group, difluoromethyl group, fluoromethyl group, chloromethyl group and bromomethyl group; the (C1–C6 alkoxy)carbonyl group represented by $R^{32}$, $R^{33}$ and $R^{34}$ may include methoxycarbonyl group, ethoxycarbonyl group, propoxycarbonyl group and isopropoxycarbonyl group; the (C3–C8 cycloalkoxy)carbonyl group represented by $R^{32}$, $R^{33}$ and $R^{34}$ may include cyclopropoxycarbonyl group, cyclobutoxycarbonyl group, cyclopentyloxycarbonyl group and cycloheyloxycarbonyl group; the (C3–C6 alkenyloxy)carbonyl group represented by $R^{32}$, $R^{33}$ and $R^{34}$ may include allyloxycarbonyl group, 1-methyl-2-propenyloxycarbonyl group and 2-methyl-2-propenyloxycarbonyl group; the (C3–C6 alkynyloxy)carbonyl group represented by $R^{32}$, $R^{33}$ and $R^{34}$ may include propargyloxycarbonyl group, 1-methyl-2-propynyloxycarbonyl group and 2-butynyloxycarbonyl group; the carboxy C1–C3 alkyl group represented by $R^{32}$, $R^{33}$ and $R^{34}$ may include carboxymethyl group, 1-carboxyethyl group and 1-methyl-1-(carboxy)ethyl group; the (C1–C6 alkoxy)carbonyl C1–C3 alkyl group represented by $R^{32}$, $R^{33}$ and $R^{34}$ may include methoxycarbonylmethyl group, ethoxycarbonylmethyl group, propoxycarbonylmethyl group, isopropoxycarbonylmethyl group, butoxycarbonylmethyl group, isobutoxycarbonylmethyl group, sec-butoxycarbonylmethyl group, tert-butoxycarbonylmethyl group, pentyloxycarbonylmethyl group, isopentyloxycarbonylmethyl group, hexyloxycarbonylmethyl group, isohexyloxycarbonylmethyl group, 1-methoxycarbonylethyl group, 1-ethoxycarbonylethyl group, 1-(propoxycarbonyl)ethyl group, 1-(isopropoxycarbonyl)ethyl group, 1-(butoxycarbonyl)ethyl group, 1-(isobutoxycarbonyl)ethyl group, 1-(sec-butoxycarbonyl)ethyl group, 1-(tert-butoxycarbonyl)ethyl group, 1-(pentyloxycarbonyl)ethyl group, 1-(isopentyloxycarbonyl)ethyl group, 1-(hexyloxycarbonyl)ethyl group, 1-(isohexyloxycarbonyl)ethyl group, 1-methyl-1-(methoxycarbonyl)ethyl group, 1-methyl-1-(ethoxycarbonyl)ethyl group, 1-methyl-1-(propoxycarbonyl)ethyl group, 1-methyl-1-(isopropoxycarbonyl)ethyl group, 1-methyl-1-(butoxycarbonyl)ethyl group, 1-methyl-1-(isobutoxycarbonyl)ethyl group, 1-methyl-1-(sec-butoxycarbonyl)ethyl group, 1-methyl-1-(tert-butoxycarbonyl)ethyl group, 1-methyl-1-(pentyloxycarbonyl)ethyl group, 1-methyl-1-(isopentyloxycarbonyl)ethyl group, 1-methyl-1-(hexyloxycarbonyl)ethyl group and 1-methyl-1-(isohexyloxycarbonyl)ethyl group; the (C3–C8 cycloalkoxy)carbonyl C1–C3 alkyl group represented by $R^{32}$, $R^{33}$ and $R^{34}$ may include cyclopropoxycarbonylmethyl group, cyclobutoxycarbonylmethyl group, cyclopentyloxycarbonylmethyl group, cyclohexyloxycarbonylmethyl group, 1-cyclopropoxycarbonylethyl group, 1-cyclobutoxycarbonylethyl group, 1-cyclopentyloxycarbonylethyl group, 1-cyclohexyloxycarbonylethyl group, 1-methyl-1-(cyclopropoxycarbonyl)ethyl group, 1-methyl-1-(cyclobutoxycarbonyl) ethyl group, 1-methyl-1-(cyclopentyloxycarbonyl)ethyl group and 1-methyl-1-(cyclohexyloxycarbonyl)ethyl group; the (C3–C6 alkenyloxy)carbonyl C1–C3 alkyl group represented by $R^{32}$, $R^{33}$ and $R^{34}$ may include allyloxycarbonylmethyl group, 1-methyl-2-propenyloxycarbonylmethyl group, 2-methyl-2-propenyloxycarbonylmethyl group, 1,1-dimethyl-2-propenyloxycarbonylmethyl group, 1-(allyloxycarbonyl)ethyl group, 1-(1-methyl-2-propenyloxycarbonyl)ethyl group, 1-(2-methyl-2-propenyloxycarbonyl)ethyl group, 1-(1,1-dimethyl-2-propenyloxycarbonyl)ethyl group, 1-methyl-1-(allyloxycarbonyl)ethyl group, 1-methyl-1-(1-methyl-2-propenyloxycarbonyl)ethyl group, 1-methyl-1-(2-methyl-2-propenyloxycarbonyl)ethyl group and 1-methyl-1-(1,1-dimethyl-2-propenyloxycarbonyl)ethyl group; the (C3–C6 alkynyloxy)carbonyl C1–C3 alkyl group represented by $R^{32}$, $R^{33}$ and $R^{34}$ may include propargyloxycarbonylmethyl group, 1-methyl-2-propynyloxycarbonylethyl group, 2-butynyloxycarbonylmethyl group, 1,1-dimethyl-2-propynyloxycarbonylmethyl group, 1-(propargyloxycarbonyl)ethyl group, 1-(1-methyl-2-propynyloxycarbonyl)ethyl group, 1-(2-butynyloxycarbonyl)ethyl group, 1-(1,1-dimethyl-2-propynyloxycarbonyl)ethyl group, 1-methyl-1-(propargyloxycarbonyl)ethyl group, 1-methyl-1-(1-methyl-2-propynyloxycarbonyl)ethyl group, 1-methyl-1-(2-butynyloxycarbonyl)ethyl group and 1-methyl-1-(1,1-dimethyl-2-propynyloxycarbonyl)ethyl group; the carboxy C1–C3 alkoxy group represented by $R^{32}$, $R^{33}$ and $R^{34}$ may include carboxymethoxy group, 1-carboxyethoxy group and 1-methyl-1-(carboxy)ethoxy group; the (C1–C6 alkoxy)carbonyl C1–C3 alkoxy group represented by $R^{32}$, $R^{33}$ and $R^{34}$ may include methoxycarboxymethoxy group, ethoxycarboxymethoxy group, propoxycarboxymethoxy group, isopropoxycarboxymethoxy group, butoxycarboxymethoxy group, isobutoxycarboxymethoxy group, sec-butoxycarboxymethoxy group, tert-butoxycarboxymethoxy group, pentyloxycarboxymethoxy group, isopentyloxycarboxymethoxy group, hexyloxycarboxymethoxy group, isohexyloxycarboxymethoxy group, 1-methoxycarboxyethoxy group, 1-ethoxycarboxyethoxy group, -(propoxycarboxy)ethoxy group, 1-(isopropoxycarboxy)ethoxy group, 1-(butoxycarboxy)ethoxy group, 1-(isobutoxycarboxy)ethoxy group, 1-(sec-butoxycarboxy)ethoxy group, 1-(tert-butoxycarboxy)ethoxy group, 1-(pentyloxycarboxy)ethoxy group, 1-(isopentyloxycarboxy)ethoxy group, 1-(hexyloxycarboxy)ethoxy group, 1-(isohexyloxycarboxy)ethoxy group, 1-methyl-1-(methoxycarboxy)ethoxy group, 1-methyl-1-(ethoxycarboxy)ethoxy group, 1-methyl-1-(propoxycarboxy)ethoxy group, 1-methyl-1-(isopropoxycarboxy)ethoxy group, 1-methyl-1-(butoxycarboxy)ethoxy group, 1-methyl-1-(isobutoxycarboxy)ethoxy group, 1-methyl-1-(sec-butoxycarboxy)ethoxy group, 1-methyl-1-(tert-butoxycarboxy)ethoxy group, 1-methyl-1-(pentyloxycarboxy)ethoxy group, 1-methyl-1-(isopentyloxycarboxy)ethoxy group, 1-methyl-1-(hexyloxycarboxy)ethoxy group and 1-methyl-1-(isohexyloxycarboxy)ethoxy group; the (C3–C8 cycloalkoxy)carbonyl C1–C3 alkoxy group represented by $R^{32}$, $R^{33}$ and $R^{34}$ may include cyclopropoxycarbonylmethoxy group, cyclobutoxycarbonylmethoxy group, cyclopentyloxycarbonylmethoxy group, cyclohexyloxycarbonylmethoxy group, 1-cyclopropoxycarbonylethoxy group, 1-cyclobutoxycarbonylethoxy group, 1-cyclopentyloxycarbonylethoxy group, 1-cyclohexyloxycarbonylethoxy group, 1-methyl-1-(cyclopropoxycarbonyl)ethoxy group, 1-methyl-1-(cyclobutoxycarbonyl)ethoxy group, 1-methyl-1-(cyclopentyloxycarbonyl)ethoxy group and 1-methyl-1-(cyclohexyloxycarbonyl)ethoxy group; the (C3–C6 alkenyloxy)carbonyl C1–C3 alkoxy group represented by $R^{32}$, $R^{33}$ and $R^{34}$ may include allyloxycarbonylmethoxy group, 1-methyl-2-propenyloxycarbonylmethoxy group, 2-methyl-2-propenyloxycarbonylmethoxy group, 1,1-dimethyl-2-propenyloxycarbonylmethoxy group, 1-(allyloxycarbonyl)ethoxy group, 1-(1-methyl-2-propenyloxycarbonyl)ethoxy group, 1-(2-methyl-2-propenyloxycarbonyl)ethoxy group, 1-(1,1-dimethyl-2-propenyloxycarbonyl)ethoxy group, 1-methyl-1-(allyloxycarbonyl)ethoxy group, 1-methyl-1-(1-methyl-2-propenyloxycarbonyl)ethoxy group, 1-methyl-1-(2-methyl-2-propenyloxycarbonyl)ethoxy group and 1-methyl-1-(1,1-dimethyl-2-propenyloxycarbonyl)ethoxy group; the (C3–C6 alkynyloxy)carbonyl C1–C3 alkoxy group represented by $R^{32}$, $R^{33}$ and $R^{34}$ may include propargyloxycarbonylmethoxy group, 1-methyl-2-propynyloxycarbonylmethoxy group, 2-butynyloxycarbonylmethoxy group, 1,1-dimethyl-2-propynyloxycarbonylmethoxy group, 1-(propargyloxycarbonyl)ethoxy group, 1-(1-methyl-2-propynyloxycarbonyl)ethoxy group, 1-(2-butynyloxycarbonyl)ethoxy group, 1-(1,1-dimethyl-2-propynyloxycarbonyl)ethoxy group, 1-methyl-1-(propargyloxycarbonyl)ethoxy group, 1-methyl-1-(1-methyl-2-propynyloxycarbonyl)ethoxy group, 1-methyl-1-(2-butynyloxycarbonyl)ethoxy group and 1-methyl-1-(1,1-dimethyl-2-propynyloxycarbonyl)ethoxy group; the carboxyl C1–C3 alkylthio group represented by $R^{32}$, $R^{33}$ and $R^{34}$ may include carboxymethylthio group, 1-carboxyethylthio group and 1-methyl-1-(carboxy)ethylthio group; the (C1–C6 alkoxy)carbonyl C1–C3 alkylthio group represented by $R^{32}$, $R^{33}$ and $R^{34}$ may include methoxycarbonylmethylthio group, ethoxycarbonylmethylthio group, propoxycarbonylmethylthio group, isopropoxycarbonylmethylthio group, butoxycarbonylmethylthio group, isobutoxycarbonylmethylthiogroup, sec-butoxycarbonylmethylthio group, tert-butoxycarbonylmethylthio group, pentyloxycarbonylmethylthio group, isopentyloxycarbonylmethylthio group, hexyloxycarbonylmethylthio group, isohexyloxycarbonylmethylthio group, 1-(methoxycarbonyl)ethylthio group, 1-(ethoxycarbonyl)ethylthio group, 1-(propoxycarbonyl)ethylthio group, 1-(isopropoxycarbonyl)ethylthio group, 1-(butoxycarbonyl)ethylthio group, 1-(isobutoxycarbonyl)ethylthio group, 1-(sec-butoxycarbonyl)ethylthio group, 1-(tert-butoxycarbonyl)ethylthio group, 1-(pentyloxycarbonyl)ethylthio group, 1-(isopentyloxycarbonyl)ethylthio group, 1-(hexyloxycarbonyl)ethylthio group, 1-(isohexyloxycarbonyl)ethylthio group, 1-methyl-1-(methoxycarbonyl)ethylthio group, 1-methyl-1-(ethoxycarbonyl)ethylthio group, 1-methyl-1-(propoxycarbonyl)ethylthio group, 1-methyl-1-(isopropoxycarbonyl)ethylthio group, 1-methyl-1-(butoxycarbonyl)ethylthio group, 1-methyl-1-(isobutoxycarbonyl)ethylthio group, 1-methyl-1-(sec-butoxycarbonyl)ethylthio group, 1-methyl-1-(tert-butoxycarbonyl)ethylthio group, 1-methyl-1-(pentyloxycarbonyl)ethylthio group, 1-methyl-1-(isopentyloxycarbonyl)ethylthio group, 1-methyl-1-(hexyloxycarbonyl)ethylthio group and 1-methyl-1-(isohexyloxycarbonyl)ethylthio group; the (C3–C8 cycloalkoxy)carbonyl C1–C3 alkylthio group represented by $R^{32}$, $R^{33}$ and $R^{34}$ may include cyclopropoxycarbonylmethylthio group, cyclobutoxycarbonylmethylthio group, cyclopentyloxycarbonylmethylthio group, cyclohexyloxycarbonylmethylthio group, 1-cyclopropoxycarbonylethylthio group, 1-cyclobutoxycarbonylethylthio group, 1-cyclopentyloxycarbonylethylthio group, 1-cyclohexyloxycarbonylethylthio group, 1-methyl-1-(cyclopropoxycarbonyl)ethylthio group, 1-methyl-1-(cyclobutoxycarbonyl)ethylthio group, 1-methyl-1-(cyclopentyloxycarbonyl)ethylthio group and 1-methyl-1-(cyclohexyloxycarbonyl)ethylthio group; the (C3–C6 alkenyloxy)carbonyl C1–C3 alkylthio group represented by $R^{32}$, $R^{33}$ and $R^{34}$ may include allyloxycarbonylmethylthio group, 1-methyl-2-propenyloxycarbonylmethylthio group, 2-methyl-2-propenyloxycarbonylmethylthio group, 1,1-dimethyl-2-propenyloxycarbonylmethylthio group, 1-(allyloxycarbonyl)ethylthio group, 1-(1methyl-2-propenyloxycarbonyl)ethylthio group, 1-(2-methyl-2-propenyloxycarbonyl)ethylthio group, 1-(1,1-dimethyl-2-propenyloxycarbonyl)ethylthio group, 1-methyl-1-(allyloxycarbonyl)ethylthio group, 1-methyl-1-(1-methyl-2-propenyloxycarbonyl)ethylthio group, 1-methyl-1-(2-methyl-2-propenyloxycarbonyl)ethylthio group and 1-methyl-1-(1,1-dimethyl-2-propenyloxycarbonyl)ethylthio group; the (C3–C6 alkynyloxy)carbonyl C1–C3 alkylthio group represented by $R^{32}$, $R^{33}$ and $R^{34}$ may include propargyloxycarbonylmethylthio group, 1-methyl-2-propynyloxycarbonylmethylthio group, 2-butynyloxycarbonylmethylthio group, 1,1-dimethyl-2-propynyloxycarbonylmethylthio group, 1-(propargyloxycarbonyl)ethylthio group, 1-(1-methyl-2-propynyloxycarbonyl)ethylthio group, 1-(2-butynyloxycarbonyl)ethylthio group, 1-(1,1-dimethyl-2-propynyloxycarbonyl)ethylthio group, 1-methyl-1-(1propargyloxycarbonyl)ethylthio group, 1-methyl-1-(1-methyl-2-propynyloxycarbonyl)ethylthio group, 1-methyl-1-(2-butynyloxycarbonyl)ethylthio group and 1-methyl-1-(1,1-dimethyl-2-propynyloxycarbonyl)ethylthio group; the C1–C6 alkoxy group represented by $R^{32}$, $R^{33}$ and $R^{34}$ may include methoxy group, ethoxy group and isopropoxy group; the C3–C6 alkenyloxy group represented by $R^{32}$, $R^{33}$ and $R^{34}$ may include allyl group; the C3–C6 alkynyloxy group represented by $R^{32}$, $R^{33}$ and $R^{34}$ may include propargyl group; the (C1–C6 alkyl)carbonyloxy group represented by $R^{32}$, $R^{33}$ and $R^{34}$ may include acetoxy group; the (C1–C6 alkoxy)carbonyloxy group represented by $R^{32}$, $R^{33}$ and $R^{34}$ may include methoxycarbonyloxy group and ethoxycarbonyloxy group; the C1–C6 alkylthio group represented by $R^{32}$, $R^{33}$ and $R^{34}$ may include methylthio group, ethylthio group and isopropylthio group; the C3–C6 alkenylthio group represented by $R^{32}$, $R^{33}$ and $R^{34}$ may include allylthio group; the C3–C6 alkynylthio group represented by $R^{32}$, $R^{33}$ and $R^{34}$ may include propargylthio group; the (C1–C6 alkyl)carbonylthio group represented by $R^{32}$, $R^{33}$ and $R^{34}$ may include acetylthio group; the (C1–C6 alkoxy)carbonylthio group represented by $R^{32}$, $R^{33}$ and $R^{34}$ may include methoxycarbonylthio group.

Some of the uracil compounds represented by the formula [V] which are obtainable according to the process of the present invention are listed in Tables 1–9 below.

Compounds given by the formula [V-1]:

TABLE 1

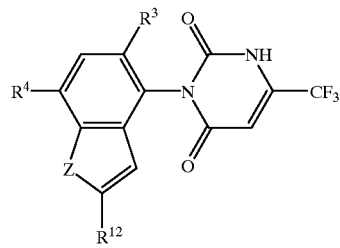

[V-1]

| Compound Nos. | Z | $R^3$ | $R^4$ | $R^{12}$ |
|---|---|---|---|---|
| 1-1 | O | F | Cl | H |
| 1-2 | O | F | Cl | $CO_2CH_3$ |
| 1-3 | O | F | Cl | $CO_2C_2H_5$ |
| 1-4 | O | F | Cl | $CO_2CH(CH_3)_2$ |
| 1-5 | O | F | Cl | $CO_2(CH_2)_3CH_3$ |
| 1-6 | O | F | Cl | $CO_2(CH_2)_4CH_3$ |
| 1-7 | O | Cl | Cl | H |
| 1-8 | O | Cl | Cl | $CO_2CH_3$ |
| 1-9 | O | Cl | Cl | $CO_2C_2H_5$ |
| 1-10 | O | Cl | Cl | $CO_2CH(CH_3)_2$ |
| 1-11 | O | Cl | Cl | $CO_2(CH_2)_3CH_3$ |
| 1-12 | O | Cl | Cl | $CO_2(CH_2)_4CH_3$ |
| 1-13 | O | F | Cl | $CH_2OCH_3$ |
| 1-14 | O | H | Cl | H |
| 1-15 | O | H | Cl | $CO_2CH_3$ |
| 1-16 | O | H | Cl | $CO_2C_2H_5$ |
| 1-17 | O | H | Cl | $CO_2CH(CH_3)_2$ |
| 1-18 | O | H | Cl | $CO_2(CH_2)_3CH_3$ |
| 1-19 | O | H | Cl | $CO_2(CH_2)_4CH_3$ |
| 1-20 | S | F | Cl | H |
| 1-21 | S | F | Cl | $CO_2CH_3$ |
| 1-22 | S | F | Cl | $CO_2C_2H_5$ |
| 1-23 | S | F | Cl | $CO_2CH(CH_3)_2$ |

Compounds given by the formula [V-2]:

TABLE 2

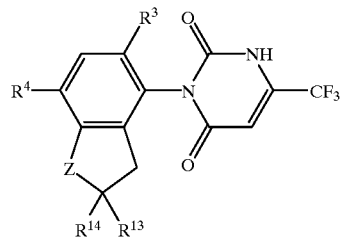

[V-2]

| Compound Nos. | Z | $R^3$ | $R^4$ | $R^{13}$ | $R^{14}$ |
|---|---|---|---|---|---|
| 2-1 | O | F | Cl | H | H |
| 2-2 | O | F | Cl | H | $CO_2CH_3$ |
| 2-3 | O | F | Cl | H | $CO_2C_2H_5$ |
| 2-4 | O | F | Cl | H | $CO_2CH(CH_3)_2$ |
| 2-5 | O | F | Cl | H | $CO_2(CH_2)_3CH_3$ |
| 2-6 | O | F | Cl | H | $CO_2(CH_2)_4CH_3$ |
| 2-7 | O | F | Cl | $CH_3$ | H |
| 2-8 | O | F | Cl | $CH_3$ | $CO_2CH_3$ |
| 2-9 | O | F | Cl | $CH_3$ | $CO_2C_2H_5$ |
| 2-10 | O | F | Cl | $CH_3$ | $CO_2CH(CH_3)_2$ |
| 2-11 | O | F | Cl | $CH_3$ | $CO_2(CH_2)_3CH_3$ |
| 2-12 | O | F | Cl | $CH_3$ | $CO_2(CH_2)_4CH_3$ |
| 2-13 | O | F | Cl | $CH_3$ | $CH_2OC(=O)CH_3$ |
| 2-14 | O | H | Cl | H | H |
| 2-15 | O | H | Cl | H | $CO_2CH_3$ |
| 2-16 | O | H | Cl | H | $CO_2C_2H_5$ |

TABLE 2-continued

[V-2]

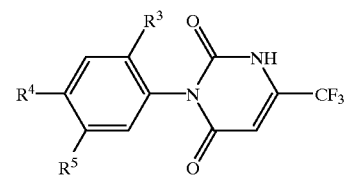

| Compound Nos. | Z | $R^3$ | $R^4$ | $R^{13}$ | $R^{14}$ |
|---|---|---|---|---|---|
| 2-17 | O | H | Cl | H | $CO_2CH(CH_3)_2$ |
| 2-18 | O | H | Cl | H | $CO_2(CH_2)_3CH_3$ |
| 2-19 | O | H | Cl | H | $CO_2(CH_2)_4CH_3$ |
| 2-20 | O | H | Cl | $CH_3$ | H |
| 2-21 | O | H | Cl | $CH_3$ | $CO_2CH_3$ |
| 2-22 | O | H | Cl | $CH_3$ | $CO_2C_2H_5$ |
| 2-23 | O | H | Cl | $CH_3$ | $CO_2CH(CH_3)_2$ |

Compounds given by the formula [V-3]:

TABLE 3

[V-3]

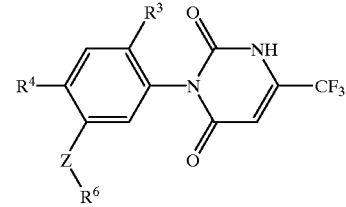

| Compound Nos. | Z | $R^3$ | T | $R^{15}$ |
|---|---|---|---|---|
| 3-1 | O | F | $CH_2$ | $CH_3$ |
| 3-2 | O | F | $CH_2$ | $CH(CH_3)_2$ |
| 3-3 | O | F | $CH_2$ | $CH_2C\equiv CH$ |
| 3-4 | O | F | $CH_2$ | $CH(CH_3)C\equiv CH$ |
| 3-5 | O | F | $CH_2$ | $CH_2CH=CH_2$ |
| 3-6 | O | F | $CH_2$ | $CH_2CH_2F$ |
| 3-7 | O | F | $CH_2$ | $CH_2OCH_3$ |
| 3-8 | O | H | $CH_2$ | $CH_3$ |
| 3-9 | O | H | $CH_2$ | $CH(CH_3)_2$ |
| 3-10 | O | H | $CH_2$ | $CH_2C\equiv CH$ |
| 3-11 | O | H | $CH_2$ | $CH(CH_3)C\equiv CH$ |
| 3-12 | O | H | $CH_2$ | $CH_2CH=CH_2$ |
| 3-13 | O | H | $CH_2$ | $CH_2CH_2F$ |
| 3-14 | O | H | $CH_2$ | $CH_2OCH_3$ |
| 3-15 | S | F | bond | $CH_3$ |
| 3-16 | S | F | bond | $CH(CH_3)_2$ |
| 3-17 | S | F | bond | $CH_2C\equiv CH$ |
| 3-18 | S | F | bond | $CH(CH_3)C\equiv CH$ |
| 3-19 | S | F | bond | $CH_2CH=CH_2$ |
| 3-20 | S | F | bond | $CH_2CH_2F$ |
| 3-21 | S | F | bond | $CH_2OCH_3$ |
| 3-22 | S | F | bond | $CH(CH_3)CO_2CH_3$ |
| 3-23 | S | F | bond | $CH(CH_3)CO_2C_2H_5$ |

Compounds given by the formula [V-4]:

TABLE 4

[V-4]

| Compound Nos. | $R^3$ | $R^4$ | $R^5$ |
|---|---|---|---|
| 4-1 | F | $C\equiv CH$ | H |
| 4-2 | F | F | H |
| 4-3 | F | Cl | H |
| 4-4 | F | Br | H |
| 4-5 | F | CN | H |
| 4-6 | F | $NO_2$ | H |
| 4-7 | Cl | Cl | H |
| 4-8 | F | F | $NO_2$ |
| 4-9 | Cl | Cl | $NO_2$ |
| 4-10 | F | CN | $NO_2$ |
| 4-11 | F | CN | F |
| 4-12 | F | Br | $NO_2$ |
| 4-13 | F | F | F |
| 4-14 | Cl | Cl | Cl |
| 4-15 | H | F | $NO_2$ |
| 4-16 | H | Cl | $NO_2$ |
| 4-17 | H | Br | $NO_2$ |
| 4-18 | H | CN | $NO_2$ |
| 4-19 | H | $NO_2$ | F |

Compounds given by the formula [V-5]:

TABLE 5

[V-5]

| Compound Nos. | Z | $R^3$ | $R^4$ | $R^6$ |
|---|---|---|---|---|
| 5-1 | O | H | Cl | $CH(CH_3)_2$ |
| 5-2 | O | H | Br | $CH(CH_3)_2$ |
| 5-3 | O | H | CN | $CH(CH_3)_2$ |
| 5-4 | O | H | F | $CH(CH_3)_2$ |
| 5-5 | O | H | Cl | $CH(CH_3)CO_2CH_3$ |
| 5-6 | O | H | Cl | $CH(CH_3)CO_2C_2H_5$ |
| 5-7 | O | H | Cl | $CH_2C\equiv CH$ |
| 5-8 | O | H | Cl | $CH(CH_3)C\equiv CH$ |
| 5-9 | O | H | Cl | $CH_2CO_2CH_3$ |
| 5-10 | O | H | Cl | $CH_2CO_2C_2H_5$ |
| 5-11 | O | F | Cl | $CH_3$ |
| 5-12 | O | F | Cl | $CH(CH_3)_2$ |
| 5-13 | O | F | Cl | $CH_2CH=CH_2$ |
| 5-14 | O | F | Cl | $CH_2C\equiv CH$ |
| 5-15 | O | F | Cl | $CH(CH_3)C\equiv CH$ |
| 5-16 | O | F | Cl | $CH_2CO_2CH_3$ |
| 5-17 | O | F | Cl | $CH_2CO_2C_2H_5$ |
| 5-18 | O | F | Cl | $CH_2CO_2(CH_2)_2CH_3$ |
| 5-19 | O | F | Cl | $CH_2CO_2CH(CH_3)_2$ |
| 5-20 | O | F | Cl | $CH_2CO_2(CH_2)_3CH_3$ |
| 5-21 | O | F | Cl | $CH_2CO_2CH(CH_3)C_2H_5$ |
| 5-22 | O | F | Cl | $CH_2CO_2(CH_2)_4CH_3$ |
| 5-23 | O | F | Cl | $CH_2CO_2(CH_2)_5CH_3$ |
| 5-24 | O | F | Cl | $CH(CH_3)CO_2CH_3$ |

TABLE 5-continued

[V-5]

| Compound Nos. | Z | R³ | R⁴ | R⁶ |
|---|---|---|---|---|
| 5-25 | O | F | Cl | CH(CH₃)CO₂C₂H₅ |
| 5-26 | O | F | Cl | CH(CH₃)CO₂(CH₂)₂CH₃ |
| 5-27 | O | F | Cl | CH(CH₃)CO₂CH(CH₃)₂ |
| 5-28 | O | F | Cl | CH(CH₃)CO₂(CH₂)₃CH₃ |
| 5-29 | O | F | Cl | CH(CH₃)CO₂CH(CH₃)C₂H₅ |
| 5-30 | O | F | Cl | CH(CH₃)CO₂(CH₂)₄CH₃ |
| 5-31 | O | F | Cl | CH(CH₃)CO₂(CH₂)₅CH₃ |
| 5-32 | O | F | Cl | CH(CH₃)CO₂CH₂OCH₃ |
| 5-33 | O | F | Cl | CH(CH₃)CO₂CH₂OC₂H₅ |
| 5-34 | O | F | Cl | CH(CH₃)CO₂CH₂CH₂OCH₃ |
| 5-35 | O | F | Cl | CH(CH₃)CO₂CH₂CH₂OC₂H₅ |
| 5-36 | O | F | Cl | CH₂OCH₃ |
| 5-37 | O | F | Cl | CH₂OC₂H₅ |
| 5-38 | O | F | Cl | CH₂CH₂F |
| 5-39 | O | F | Cl | CH(CH₃)C≡CH (R-isomer) |
| 5-40 | O | F | Cl | CH(CH₃)C≡CH (S-isomer) |
| 5-41 | O | F | Cl | CH(CH₃)CO₂CH₃ (R-isomer) |
| 5-42 | O | F | Cl | CH(CH₃)CO₂CH₃ (S-isomer) |
| 5-43 | O | F | Cl | CH(CH₃)CO₂C₂H₅ (R-isomer) |
| 5-44 | O | F | Cl | CH(CH₃)CO₂C₂H₅ (S-isomer) |
| 5-45 | O | F | Cl | CH(CH₃)CO₂(CH₂)₂CH₃ (R-isomer) |
| 5-46 | O | F | Cl | CH(CH₃)CO₂(CH₂)₂CH₃ (S-isomer) |
| 5-47 | O | F | Cl | CH(CH₃)CO₂CH(CH₃)C₂H₅ (R-isomer) |
| 5-48 | O | F | Cl | CH(CH₃)CO₂CH(CH₃)C₂H₅ (S-isomer) |
| 5-49 | O | F | Cl | C₆H₄-3-(OCH₂CO₂CH₃) |
| 5-50 | O | F | Cl | C₆H₄-3-(OCH₂CO₂C₂H₅) |
| 5-51 | O | F | Cl | C₆H₄-3-(OCH₂CO₂(CH₂)₂CH₃) |
| 5-52 | O | F | Cl | C₆H₄-4-(OCH₂CO₂CH₃) |
| 5-53 | O | F | Cl | C₆H₄-4-(OCH₂CO₂C₂H₅) |
| 5-54 | O | F | Cl | C₆H₄-4-(OCH₂CO₂(CH₂)₂CH₃) |
| 5-55 | O | F | Cl | C₆H₄-3-(OCH(CH₃)CO₂CH₃) |
| 5-56 | O | F | Cl | C₆H₄-3-(OCH(CH₃)CO₂C₂H₅) |
| 5-57 | O | F | Cl | C₆H₄-3-(OCH(CH₃)CO₂(CH₂)₂CH₃) |
| 5-58 | O | F | Cl | C₆H₄-4-(OCH(CH₃)CO₂CH₃) |
| 5-59 | O | F | Cl | C₆H₄-4-(OCH(CH₃)CO₂C₂H₅) |
| 5-60 | O | F | Cl | C₆H₄-4-(OCH(CH₃)CO₂(CH₂)₂CH₃) |
| 5-61 | O | F | Cl | C₆H₄-2-(OCH₂CO₂CH₃) |

Compounds given by the formula [V-6]:

TABLE 6

[V-6]

| Compound Nos. | R³ | R⁴ | R⁷ |
|---|---|---|---|
| 6-1 | H | Cl | OCH₂CH=CH₂ |
| 6-2 | H | Cl | OCH₃ |
| 6-3 | H | Cl | OC₂H₅ |
| 6-4 | H | Cl | O(CH₂)₂CH₃ |
| 6-5 | H | Cl | OCH(CH₃)₂ |

TABLE 6-continued

[V-6]

| Compound Nos. | R³ | R⁴ | R⁷ |
|---|---|---|---|
| 6-6 | H | Cl | OCH₂CO₂CH₃ |
| 6-7 | H | Cl | OCH₂CO₂C₂H₅ |
| 6-8 | H | Cl | OCH₂CO₂CH₂CH=CH₂ |
| 6-9 | H | Cl | OCH₂CO₂CH₂C≡CH |
| 6-10 | H | Cl | OCH(CH₃)CO₂CH₃ |
| 6-11 | H | Cl | OCH(CH₃)CO₂C₂H₅ |
| 6-12 | H | Cl | OCH(CH₃)CO₂CH₂CH=CH₂ |
| 6-13 | H | Cl | OCH(CH₃)CO₂CH₂C≡CH |
| 6-14 | H | Cl | OC(CH₃)₂CO₂CH₃ |
| 6-15 | H | Cl | OC(CH₃)₂CO₂C₂H₅ |
| 6-16 | H | Cl | OC(CH₃)₂CO₂CH₂CH=CH₂ |
| 6-17 | H | Cl | OC(CH₃)₂CO₂CH₂C≡CH |
| 6-18 | F | Cl | OCH₂CH=CH₂ |
| 6-19 | F | Cl | OCH(CH₃)₂ |
| 6-20 | F | Cl | OCH₂CO₂CH₂CH=CH₂ |
| 6-21 | F | Cl | OCH₂CO₂CH₂C≡CH |
| 6-22 | F | Cl | OC(CH₃)₂CO₂CH₂CH=CH₂ |
| 6-23 | F | Cl | OC(CH₃)₂CO₂CH₂C≡CH |

Compounds given by the formula [V-7]:

TABLE 7

[V-7]

| Compound Nos. | R³ | R⁴ | R⁹ | R⁸ |
|---|---|---|---|---|
| 7-1 | H | Cl | H | OCH₃ |
| 7-2 | H | Cl | H | OC₂H₅ |
| 7-3 | H | Cl | H | O(CH₂)₂CH₃ |
| 7-4 | H | Cl | H | OCH(CH₃)₂ |
| 7-5 | H | Cl | H | O(CH₂)₃CH₃ |
| 7-6 | H | Cl | H | O(CH₂)₄CH₃ |
| 7-7 | H | Cl | Cl | OCH₃ |
| 7-8 | H | Cl | Cl | OC₂H₅ |
| 7-9 | H | Cl | Cl | O(CH₂)₂CH₃ |
| 7-10 | H | Cl | Cl | OCH(CH₃)₂ |
| 7-11 | H | Cl | Cl | O(CH₂)₃CH₃ |
| 7-12 | H | Cl | Cl | O(CH₂)₄CH₃ |
| 7-13 | F | Cl | H | OCH₃ |
| 7-14 | F | Cl | H | OC₂H₅ |
| 7-15 | F | Cl | H | O(CH₂)₂CH₃ |
| 7-16 | F | Cl | H | OCH(CH₃)₂ |
| 7-17 | F | Cl | H | O(CH₂)₃CH₃ |
| 7-18 | F | Cl | Cl | OCH₃ |
| 7-19 | F | Cl | Cl | OC₂H₅ |
| 7-20 | F | Cl | Cl | O(CH₂)₂CH₃ |
| 7-21 | F | Cl | Cl | OCH(CH₃)₂ |
| 7-22 | F | Cl | Cl | O(CH₂)₃CH₃ |
| 7-23 | F | Cl | Cl | O(CH₂)₄CH₃ |

Compounds given by the formula [V-8]:

TABLE 8

[V-8]

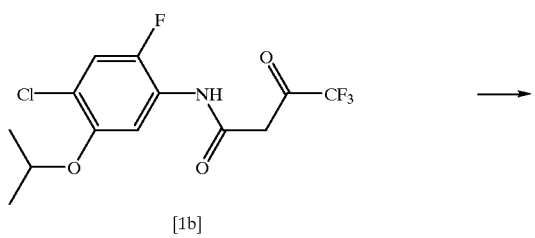

| Compound Nos. | $R^3$ | $R^4$ | $R^{11}$ | $R^{10}$ |
|---|---|---|---|---|
| 8-1 | H | Cl | H | $OCH_3$ |
| 8-2 | H | Cl | H | $OC_2H_5$ |
| 8-3 | H | Cl | H | $O(CH_2)_2CH_3$ |
| 8-4 | H | Cl | H | $OCH(CH_3)_2$ |
| 8-5 | H | Cl | H | $O(CH_2)_3CH_3$ |
| 8-6 | H | Cl | H | $O(CH_2)_4CH_3$ |
| 8-7 | H | Cl | Cl | $OCH_3$ |
| 8-8 | H | Cl | Cl | $OC_2H_5$ |
| 8-9 | H | Cl | Cl | $O(CH_2)_2CH_3$ |
| 8-10 | H | Cl | Cl | $OCH(CH_3)_2$ |
| 8-11 | H | Cl | Cl | $O(CH_2)_3CH_3$ |
| 8-12 | H | Cl | Cl | $O(CH_2)_4CH_3$ |
| 8-13 | F | Cl | H | $OCH_3$ |
| 8-14 | F | Cl | H | $OC_2H_5$ |
| 8-15 | F | Cl | H | $O(CH_2)_2CH_3$ |
| 8-16 | F | Cl | H | $OCH(CH_3)_2$ |
| 8-17 | F | Cl | H | $O(CH_2)_3CH_3$ |
| 8-18 | F | Cl | Cl | $OCH_3$ |
| 8-19 | F | Cl | Cl | $OC_2H_5$ |
| 8-20 | F | Cl | Cl | $O(CH_2)_2CH_3$ |
| 8-21 | F | Cl | Cl | $OCH(CH_3)_2$ |
| 8-22 | F | Cl | Cl | $O(CH_2)_3CH_3$ |
| 8-23 | F | Cl | Cl | $O(CH_2)_4CH_3$ |

EXAMPLES

Hereinafter, the present invention is explained in more detail, but the present invention is not limited to the following examples.

Production Example 1

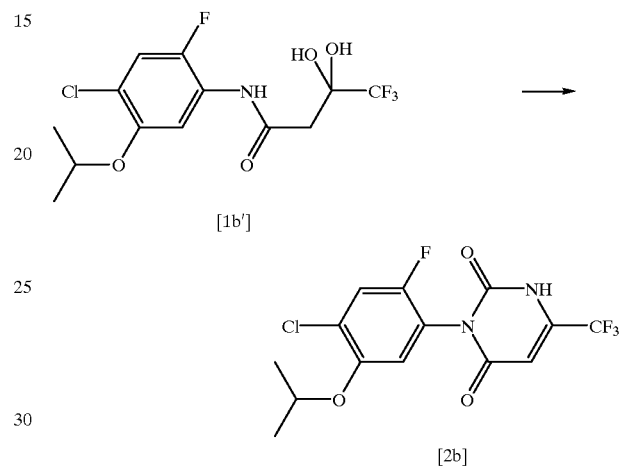

To a mixture of 1.0 g of Compound [1b] and 10 mL of acetic acid, 0.25 g of potassium cyanate was added and stirred for 3 hours at room temperature. After heated under reflux of acetic acid for 3 hours, the reaction mixture was poured into water and extracted with ethyl acetate. The organic layer was washed with aqueous sodium bicarbonate, dried over anhydrous magnesium sulfate and concentrated. The obtained solid was washed with hexane and t-butyl methy ether (v/v=2/1) and water subsequently, and dried to give 1.01 g of Compound [2b].

Compound [2b]

$^1$H-NMR (300 MHz, $CDCl_3$+DMSO-$d_6$, TMS δ (ppm)) 1.36 (6H,d,J=6.12 Hz), 4.45 (1H,qi,J=6.12 Hz), 6.10 (1H,s), 6.84 (1H,d,J=6.68 Hz), 7.25 (1H,d,J=8.87 Hz)

Production Example 2

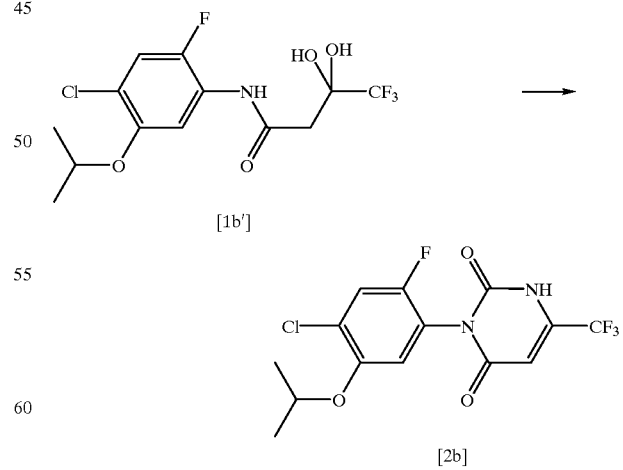

To a mixture of 2.0 g of Compound [1b'] and 10 mL of acetic acid, 0.6 g of potassium cyanate was added at room temperature, stirred for 8 hours and allowed to stand overnight. Then, the mixture was heated under reflux of acetic acid for 3 hours, and concentrated. The obtained solid was washed with a mixture of hexane and t-butyl methyl ether (v/v=2/1) and water subsequently, and dried to give 2.11 g of Compound [2b].

Production Example 3

To a mixture of 3.16 g of Compound [1b'] and 13.8 mL of toluene, 0.79 g of sodium cyanate was added at room temperature, and stirred at 80° C. for 40 minutes. Then, 5 mL of acetic acid was added to the mixture, and stirred at 80° C. for 80 minutes and at 100° C. for 110 minutes, respectively. After allowing to stand overnight at room temperature, the mixture was stirred at 100° C. for 6 hours and 40 minutes. Water was added to the reaction solution and the solution was extracted with ethyl acetate, neutralized with aqueous sodium hydroxide and washed with saturated brine. The organic layer was dried over anhydrous magnesium sulfate and concentrated. The obtained solid was washed with hexane and dried to give 1.67 g of Compound [2b].

Production Example 4

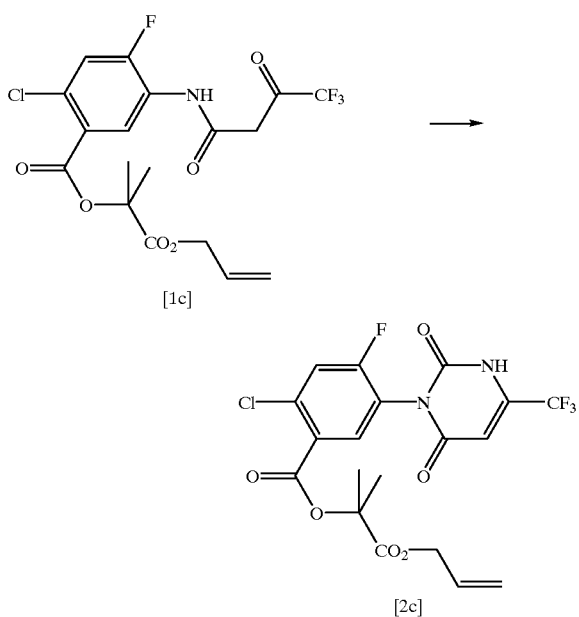

To a mixture of 2.55 g of Compound [1c] and 8 mL of acetic acid, 0.63 g of potassium cyanate was added at room temperature, and stirred for 9 hours. Then, allowed to stand at room temperature overnight, stirred for 12 hours, allowed to stand at room temperature overnight, stirred for 12 hours, allowed to stand at room temperature, stirred for 11 hours and further allowed to stand for 3 days. After that, the mixture was heated under reflux of acetic acid for 12 hours, allowed to stand at room temperature overnight, and heated under reflux of acetic acid for 4 hours. The reaction solution was concentrated, added to aqueous sodium bicarbonate and extracted with ethyl acetate. The organic layer was dried over anhydrous magnesium sulfate and concentrated. The obtained residue was subjected to column chromatography (hexane:ethyl acetate=3:2) to give 1.83 g of Compound [2c].

Compound [2c]

$^1$H-NMR (300 MHz, CDCl$_3$, TMS δ (ppm)) 1.70 (6H,s), 4.66 (2H,d,J=5.68 Hz), 5.20–5.35 (2H,m), 5.83–5.95 (1H, m), 6.26 (1H,s), 7.28–7.32 (1H,m), 7.59 (1H,d,J=8.53 Hz), 7.78 (1H,d,J=9.30 Hz)

Production Example 5

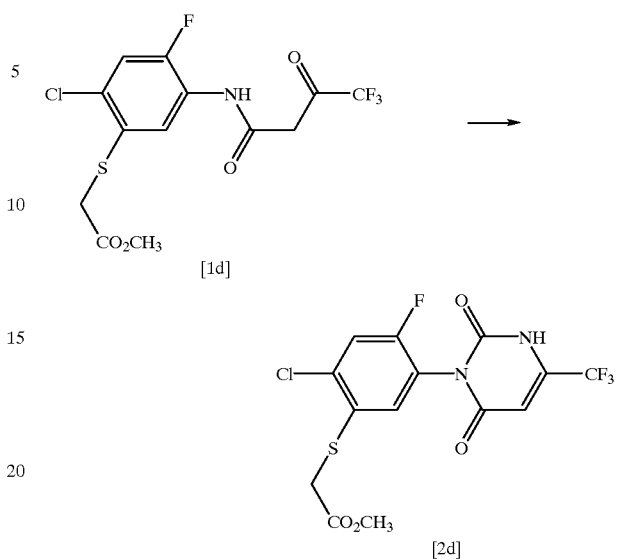

To a mixture of 3.11 g of Compound [1d] and 12 mL of acetic acid, 0.87 g of potassium cyanate was added at room temperature, and stirred for 5 hours. Then, the mixture was heated under reflux of acetic acid for 7 hours, allowed to stand at room temperature overnight, and heated under reflux of acetic acid for 6 hours. The reaction solution was concentrated, added to water and extracted with ethyl acetate. The organic layer was washed with aqueous saturated sodium bicarbonate, dried over anhydrous magnesium sulfate and concentrated. The obtained residue was subjected to column chromatography (hexane:ethyl acetate= 3:1–1:1) to give 2.04 g of Compound [2d].

Compound [2d]

$^1$H-NMR (300 MHz, CDCl$_3$, TMS δ (ppm)) 3.65 (2H,s), 3.70 (3H,s), 6.25 (1H,s), 7.36 (1H,d,J=10.8 Hz), 7.44 (1H, d,J=8.83 Hz)

Production Example 6

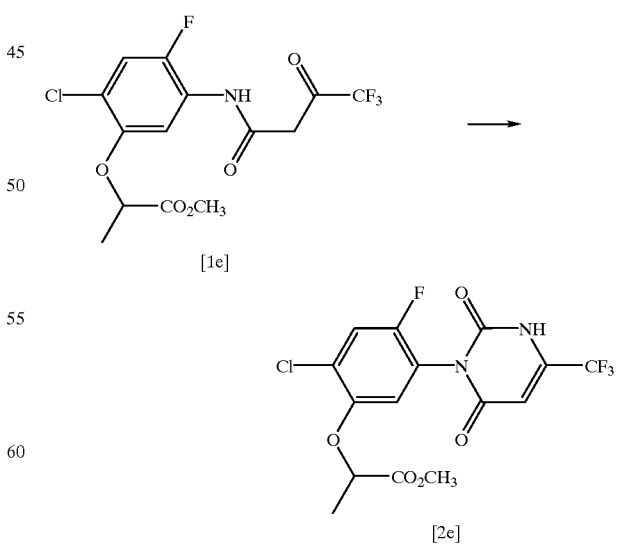

To a mixture of 3.10 g of Compound [1e] and 12 mL of acetic acid, 0.87 g of potassium cyanate was added at room temperature, stirred for 9 hours and allowed to stand overnight. Then, the mixture was heated under reflux of acetic acid for 11 hours. The reaction solution was concentrated, added to water and extracted with ethyl acetate. The organic layer was washed with aqueous saturated sodium bicarbonate, dried over anhydrous magnesium sulfate and concentrated. The obtained solid was washed with a mixture of hexane and ether (5:1) to give 1.77 g of Compound [2e].

Compound [2e]

m.p. 145.8° C.

$^1$H-NMR (300 MHz, CDCl$_3$, TMS δ (ppm)) 1.67 (3H,d, J=6.92 Hz), 3.75 (3H,s), 4.70 (1H,q,J=6.92 Hz), 6.23 (1H,s), 6.81–6.85 (1H,m), 7.32 (1H,d,J=8.92 Hz)

Production Example 7

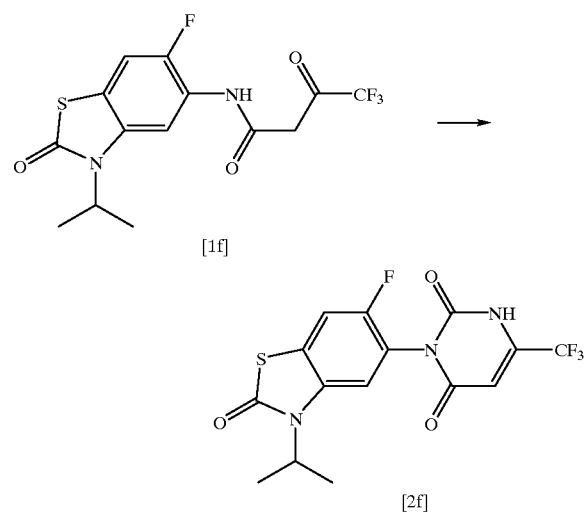

To a mixture of 3.07 g of Compound [1f] and 12 mL of acetic acid, 0.91 g of potassium cyanate was added at room temperature, and stirred for 3 hours. Then, the mixture was heated under reflux of acetic acid for 9 hours, allowed to stand at room temperature overnight, and heated under reflux of acetic acid for 2 hours. The reaction solution was concentrated, added to water and extracted with ethyl acetate. The organic layer was washed with aqueous saturated sodium bicarbonate and saturated brine respectively, dried over anhydrous magnesium sulfate and concentrated. The obtained residue was subjected to column chromatography (hexane:ethyl acetate=2:1) to give 2.36 g of Compound [2f].

Compound [2f]

$^1$H-NMR (300 MHz, CDCl$_3$, TMS δ (ppm)) 1.55 (6H,d, J=6.92 Hz), 4.68–4.77 (1H,brm), 6.28 (1H,s), 7.07 (1H,d, J=5.70 Hz), 7.35 (1H,d,J=8.51 Hz)

Production Example 8

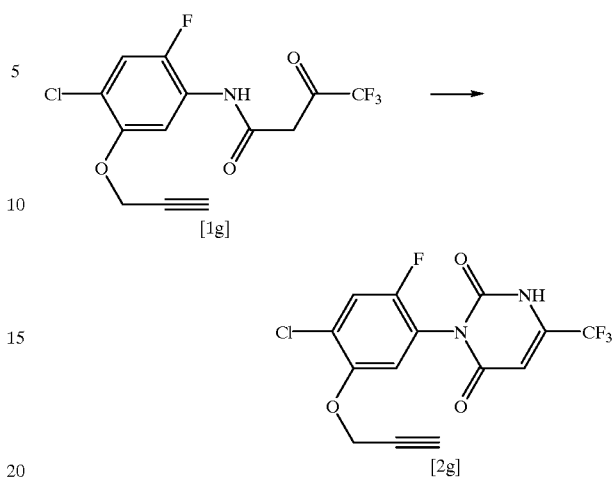

To a mixture of 2.42 g of Compound [1g] and 10 mL of acetic acid, 0.77 g of potassium cyanate was added at room temperature, stirred for 4 hours and allowed to stand at room temperature overnight. Then, the mixture was heated under reflux of acetic acid for 8 hours. The reaction solution was concentrated, added to water and extracted with ethyl acetate. The organic layer was washed with aqueous saturated sodium bicarbonate, dried over anhydrous magnesium sulfate and concentrated. The obtained residue was subjected to column chromatography (hexane:ethyl acetate= 3:1–2:1) to give 1.50 g of Compound [2g].

Compound [2g]

m.p. 151.9° C.

$^1$H-NMR (300 MHz, CDCl$_3$, TMS δ (ppm)) 2.57 (1H,t, J=2.30 Hz), 4.75 (2H,d,J=2.30 Hz), 6.26 (1H,s), 6.99 (1H, d,J=6.36 Hz), 7.34 (1H,d,J=8.77 Hz)

Production Example 9

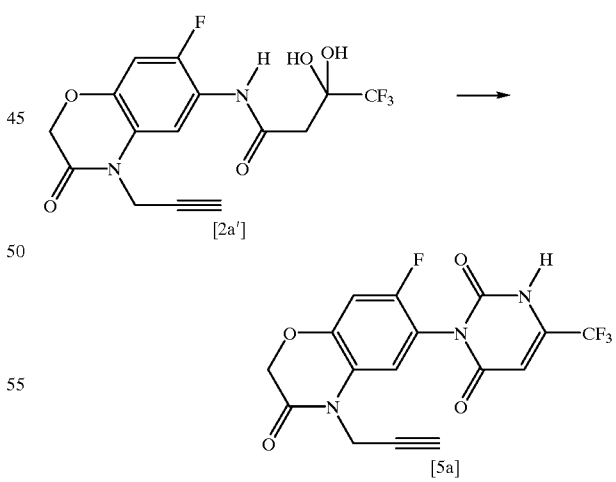

To 50 mL of acetic acid, 5.0 g of Compound [2a'] and 1.3 g of potassium cyanate were added and allowed to stand overnight at room temperature. Then, the mixture was heated under reflux of acetic acid for 4 hours, concentrated under a reduced pressure, added to water, and extracted with ethyl acetate. The organic layer was washed with aqueous sodium bicarbonate, dried over anhydrous magnesium sulfate and concentrated under a reduced pressure to give 5.1 g of Compound [5a].

Compound [5a]

$^1$H-NMR (250 MHz, CDCl$_3$, TMS δ (ppm)) 2.28–2.31 (1H,m), 4.60–4.71 (4H,m), 6.27 (1H,s), 6.94 (1H,d,J=9.4 Hz), 7.07 (1H,d,J=6.6 Hz)

Next, an example of the production method of the amide compound represented by the general formula [II] or its hydrate is shown as reference examples.

Reference Example 1

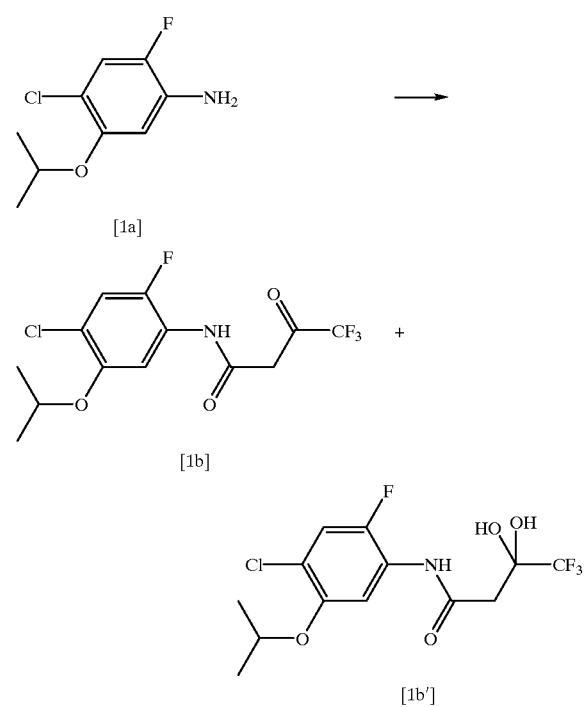

To 200 mL of toluene, 20.3 g of Compound [1a] and 20.2 g of ethyl 3,3,3-trifluoroacetoacetate were added and heated under reflux of toluene for 4 hours. Then, the reaction mixture was concentrated under a reduced pressure, subjected to silica gel column chromatography (hexane and ethyl acetate, v/v=5/1) and a fraction was concentrated under a reduced pressure to give a residue, to which hexane was added to give crystals. The crystals were collected to give 15.2 g of Compound [1b]. Another fraction gave 8.3 g of Compound [1b'] by the same procedures.

Compound [1b]

$^1$H-NMR (250 MHz, CDCl$_3$, TMS δ (ppm)) 1.33–1.42 (6H,m), 4.45–4.57 (1H,m), 5.67 (1H,s), 7.15 (1H,d,J=10.3 Hz), 7.37 (1H,bs), 7.94–8.02 (1H,m)

Compound [1b']

$^1$H-NMR (250 MHz, CDCl$_3$, TMS δ (ppm)) 1.37 (6H,d, J=6.06 Hz), 2.86 (2H,s), 4.47–4.57 (1H,m), 5.21 (2H,s), 7.16 (1H,d,J=10.3 Hz), 7.62 (1H,bs), 7.98 (1H,d,J=7.26 Hz)

m.p. 110.4° C.

Reference Example 2

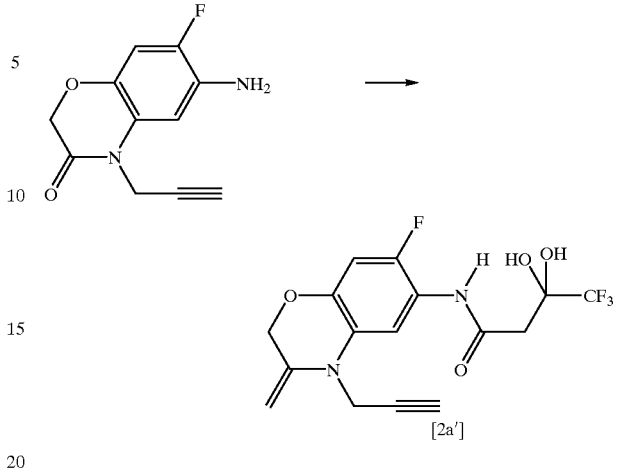

To 150 mL of toluene, 33.0 g of Compound [3a] and 30.3 g of ethyl 3,3,3-trifluoroacetoacetate were added and heated under reflux of toluene for 4 hours. Then, the reaction mixture was concentrated under a reduced pressure. The obtained crystals were dissolved with ethyl acetate, washed with conc. HCl and water subsequently, dried over anhydrous magnesium sulfate and concentrated under a reduced pressure to give 35.7 g of Compound [2a'].

Compound [2a']

m.p. 110.4° C.

What is claimed is:

1. A process for producing an uracil compound represented by the formula [V]:

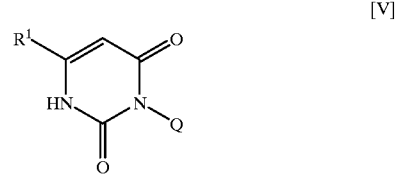

wherein R$^1$ represents C1–C5 perfluoroalkyl group and Q represents an aromatic group, which ccomprises making an amide compound represented by the formula [II]:

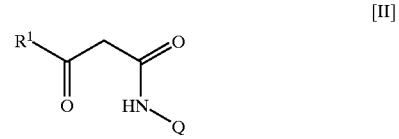

wherein R$^1$ and Q have the same meanings defined above, or its hydrate react with a cyanate salt in the presence of a protonic acid at 55° C. to 150° C.

2. A process according to claim 1, wherein R$^1$ represents trifluoromethyl group.

3. A process according to claim 1, wherein Q represents an optionally substituted phenyl group.

4. A process according to claim 1, wherein Q in the formulae [II] and [V] is any group of the general formulae Q1 to Q8 given below:

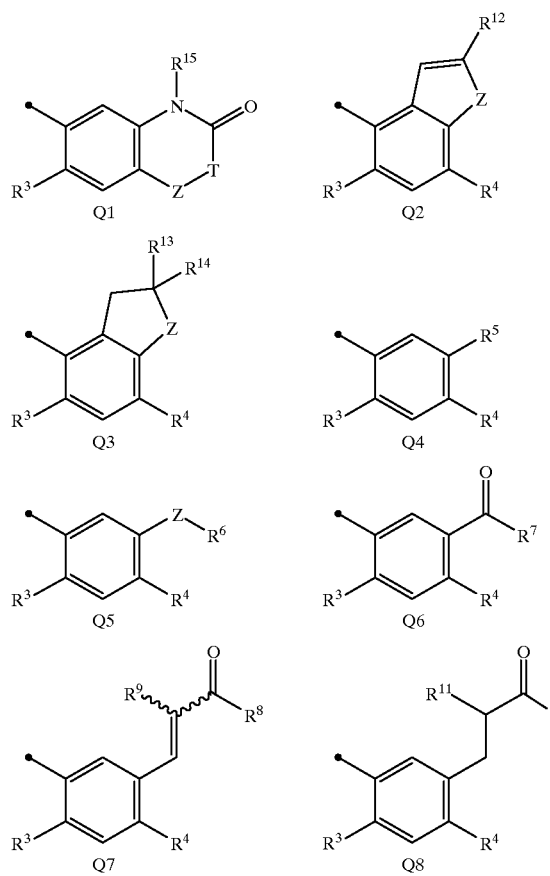

wherein $R^3$ represents hydrogen atom or halogen atom; $R^4$ represents hydrogen atom, halogen atom, cyano group, nitro group, ethynyl group or a group given by the formula:

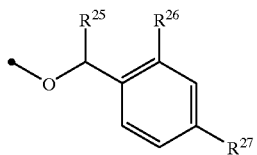

$R^5$ represents hydrogen atom, C1–C6 alkyl group, halogen atom, cyano group, nitro group or hydroxy group; $R^6$ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl)carbonyl group, (C1–C6 haloalkyl)carbonyl group, (C3–C8 cycloalkyl)carbonyl group, carboxy C1–C3 alkyl group, (C1–C6 alkoxy) carbonyl C1–C3 alkyl group, (C1–C6 haloalkoxy) carbonyl C1–C3 alkyl group, (C3–C8 cycloalkoxy) carbonyl C1–C3 alkyl group, (C3–C6 alkenyloxy) carbonyl C1–C3 alkyl group, (C3–C6 alkynyloxy) carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy) carbonyl C1–C3 alkoxycarbonyl C1–C3 alkyl group, (C1–C6 haloalkoxy)carbonyl C1–C3 alkoxycarbonyl C1–C3 alkyl group, (C3–C6 alkenyloxy)carbonyl C1–C3 alkoxycarbonyl C1–C3 alkyl group, (C3–C6 alkynyloxy)carbonyl (C1–C3 alkoxy)carbonyl C1–C3 alkyl group, (C3–C8 cycloalkoxy)carbonyl (C1–C3 alkoxy)carbonyl C1–C3 alkyl group, optionally substituted aryloxycarbonyl C1–C3 alkyl group, optionally substituted aryl (C1–C3 alkoxy)carbonyl C1–C3 alkyl group, (C1–C6 alkoxy)carbonyl group, or a group given by the formula —$SO_2R^{17}$, —$C(R^{28})R^{29}CON(R^{21})R^{22}$, —$C(R^{30})R^{31}COON(R^{23})R^{24}$,

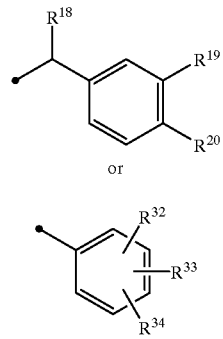

or $R^7$ represents hydrogen atom, C1–C6 alkyl group, C1–C6 haloalkyl group, C3–C8 cycloalkyl group, hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, carboxy C1–C3 alkoxy group, (C1–C6 alkoxy)carboxy C1–C3 alkoxy group, (C3–C8 cycloalkoxy)carboxy C1–C3 alkoxy group, (C3–C6 alkenyloxy)carboxy C1–C3 alkoxy group, (C3–C6 alkynyloxy)carboxy C1–C3 alkoxy group, optionally substituted phenoxy group, optionally substituted benzyloxy group, or a group given by the formula —$N(R^{21})R^{22}$ or —$ON(R^{23})R^{24}$; $R^8$ represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the general formula —$N(R^{21})R^{22}$ or —$ON(R^{23})R^{24}$; $R^9$ represents hydrogen atom or halogen atom; $R^{10}$ represents hydroxy group, C1–C6 alkoxy group, C1–C6 haloalkoxy group, C3–C8 cycloalkoxy group, C3–C6 alkenyloxy group, C3–C6 alkynyloxy group, (C1–C3 alkoxy) C1–C3 alkoxy group, optionally substituted phenoxy group, optionally substituted benzyloxy group, or a group given by the formula —$N(R^{21})R^{22}$ or —$ON(R^{23})R^{24}$; $R^{11}$ represents hydrogen atom or halogen atom; $R^{12}$ represents hydrogen atom, formyl group, cyano group, nitro group, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy)carbonyl group, (C3–C8 cycloalkoxy)carbonyl group, (C3–C6 alkenyloxy) carbonyl group, (C3–C6 alkynyloxy)carbonyl group or C1–C3 alkoxy (C1–C3 alkoxy)carbonyl group; $R^{13}$ represents hydrogen atom or C1–C3 alkyl group; $R^{14}$ represents hydrogen atom, C1–C6 alkyl group, C1–C6 haloalkyl group, hydroxy C1–C3 alkyl group, (C1–C3 alkoxy) C1–C3 alkyl group, (C1–C6 alkyl)carbonyloxy C1–C3 alkyl group, (C1–C6 haloalkyl)carbonyloxy C1–C3 alkyl group, carboxy group, (C1–C6 alkoxy)carbonyl group, (C1–C6 haloalkoxy)carbonyl group, (C3–C8 cycloalkoxy)carbonyl group, (C3–C6 alkenyloxy)carbonyl group, (C3–C6 alkynyloxy)carbonyl group or C1–C3 alkoxy (C1–C3 alkoxy)carbonyl group; $R^{15}$ represents C1–C6 alkyl group, C1–C6 haloalkyl group, C3–C8 cycloalkyl group, (C3–C8 cycloalkyl) C1–C3 alkyl group, C3–C6 alkenyl group, C3–C6 alkynyl group, cyano C1–C3 alkyl group, (C1–C3 alkoxy) C1–C3 alkyl group, (C1–C3 alkylthio) C1–C3 alkyl group, (C1–C6 alkyl)carbonyl group, (C1–C6 haloalkyl)carbonyl group, (C3–C8 cycloalkyl)carbonyl group, carboxy C1–C3 alkyl group, (C1–C6 alkoxy)carbonyl C1–C3 alkyl group, (C1–C6 haloalkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, C1–C3 alkoxy (C1–C3 alkoxy)carbonyl C1–C3 alkyl group, carboxy (C1–C3 alkoxy)carbonyl C1–C3 alkyl group, (C1–C6 alkoxy)carbonyl (C1–C3 alkoxy)carbonyl C1–C3 alkyl group, (C1–C6 haloalkoxy)carbonyl (C1–C3 alkoxy)carbonyl C1–C3 alkyl group, (C3–C8 cycloalkoxy)carbonyl (C1–C3 alkoxy)carbonyl C1–C3 alkyl group, (C3–C6 alkenyloxy)carbonyl (C1–C3 alkoxy)carbonyl C1–C3 alkyl group, (C3–C6 alkynyloxy)carbonyl (C1–C3 alkoxy)carbonyl C1–C3 alkyl group, optionally substituted aryloxycarbonyl C1–C3 alkyl group, optionally substituted aryl (C1–C3 alkoxy)carbonyl C1–C3 alkyl group, (C1–C6 alkoxy)carbonyl group or a group given by the formula:

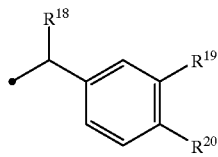

Z represents oxygen atom or sulfur atom; T represents direct bond or methylene group;

wherein $R^{17}$ represents C1–C3 alkyl group or C1–C3 haloalkyl group; $R^{18}$ represents hydrogen atom, C1–C3 alkyl group or (C1–C6 alkoxy)carbonyl group; $R^{19}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{20}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{21}$ and $R^{22}$ independently represent hydrogen atom or C1–C3 alkyl group, or combined together at their terminal ends to form C2–C5 alkylene group or (C1–C3 alkyleneoxy) C1–C3 alkylene group; $R^{23}$ and $R^{24}$ independently represent hydrogen atom or C1–C3 alkyl group, or combined together at their terminal ends to form C2–C5 alkylene group or (C1–C3 alkyleneoxy) C1–C3 alkylene group; $R^{25}$ represents hydrogen atom, C1–C3 alkyl group or C1–C6 alkoxycarbonyl group; $R^{26}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{27}$ represents hydrogen atom, halogen atom, nitro group, hydroxy group, C1–C6 alkyl group, C1–C6 haloalkyl group, C1–C6 alkoxy group, C1–C6 haloalkoxy group, C3–C8 cycloalkoxy group, C3–C6 alkenyloxy group, C3–C6 alkynyloxy group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group or (C3–C6 alkynyloxy)carbonyl C1–C3 alkoxy group; $R^{28}$ represents hydrogen atom or C1–C3 alkyl group; $R^{29}$ represents hydrogen atom or C1–C3 alkyl group; $R^{30}$ represents hydrogen atom or C1–C3 alkyl group; $R^{31}$ represents hydrogen atom or C1–C3 alkyl group; $R^{32}$, $R^{33}$ and $R^{34}$ are the same or different and represent hydrogen atom, halogen atom, C1–C3 alkyl group, C1–C3 haloalkyl group, nitro group, hydroxy group, mercapto group, cyano group, carboxy group, (C1–C6 alkoxy)carbonyl group, (C3–C8 cycloalkoxy)carbonyl group, (C3–C6 alkenyloxy)carbonyl group, (C3–C6 alkynyloxy)carbonyl group, carboxy C1–C3 alkyl group, (C1–C6 alkoxy)carbonyl C1–C3 alkyl group, (C3–C8 cycloalkoxy)carbonyl C1–C3 alkyl group, (C3–C6 alkenyloxy)carbonyl C1–C3 alkyl group, (C3–C6 alkynyloxy)carbonyl C1–C3 alkyl group, carboxy C1–C3 alkoxy group, (C1–C6 alkoxy)carbonyl C1–C3 alkoxy group, (C3–C8 cycloalkoxy)carbonyl C1–C3 alkoxy group, (C3–C6 alkenyloxy)carbonyl C1–C3 alkoxy group, (C3–C6 alkynyloxy)carbonyl C1–C3 alkoxy group, carboxy C1–C3 alkylthio group, (C1–C6 alkoxy)carbonyl C1–C3 alkylthio group, (C3–C8 cycloalkoxy)carbonyl C1–C3 alkylthio group, (C3–C6 alkenyloxy)carbonyl C1–C3 alkylthio group, (C3–C6 alkynyloxy)carbonyl C1–C3 alkylthio group, C1–C6 alkoxy group, C3–C6 alkenyloxy group, C3–C6 alkynyloxy group, (C1–C6 alkyl)carbonyloxy group, (C1–C6 alkoxy)carbonyloxy group, C1–C6 alkylthio group, C3–C6 alkenylthio group, C3–C6 alkynylthio group, (C1–C6 alkyl)carbonylthio group, (C1–C6 alkoxy)carbonylthio group.

* * * * *